(12) United States Patent
Sabir et al.

(10) Patent No.: US 10,292,972 B1
(45) Date of Patent: May 21, 2019

(54) PHARMACEUTICAL COMPOSITION FOR TREATING CANCER AND A METHOD THEREOF

(71) Applicant: King Abdulaziz University, Jeddah (SA)

(72) Inventors: Jamal Sabir M. Sabir, Jeddah (SA); Abdullah Y. Obaid, Jeddah (SA); Nahid H. Hajrah, Jeddah (SA); Waseem Mohammed, Jeddah (SA); Zainab H. Abdul-Hameed, Al-Madina (SA); Walied M. Alarif, Jeddah (SA); Roop Singh Bora, Jeddah (SA); Seif-Eldin N. Ayyad, Mansoura (EG); Nouf Saeed A. Al-Abbas, Jeddah (SA); Abdulkader M. Shaikh Omer, Jeddah (SA); Mohammed Zainy Mutawakil, Jeddah (SA); Neil Hall, Wymondham (GB); Kulvinder Singh Saini, Melbourne (AU)

(73) Assignee: King Abdulaziz University, Jeddah (SA)

( * ) Notice: Subject to any disclaimer, the term of this patent is extended or adjusted under 35 U.S.C. 154(b) by 42 days.

(21) Appl. No.: 15/794,665

(22) Filed: Oct. 26, 2017

(51) Int. Cl.
| | | |
|---|---|---|
| *A61K 31/439* | (2006.01) | |
| *C07D 498/22* | (2006.01) | |
| *A61K 36/24* | (2006.01) | |
| *B01D 11/02* | (2006.01) | |
| *B01D 15/12* | (2006.01) | |
| *B01D 15/42* | (2006.01) | |

(52) U.S. Cl.
CPC .......... *A61K 31/439* (2013.01); *A61K 36/24* (2013.01); *B01D 11/0288* (2013.01); *B01D 11/0292* (2013.01); *B01D 15/12* (2013.01); *B01D 15/426* (2013.01); *C07D 498/22* (2013.01); *A61K 2236/15* (2013.01); *A61K 2236/17* (2013.01); *A61K 2236/35* (2013.01); *A61K 2236/51* (2013.01); *A61K 2236/55* (2013.01)

(58) Field of Classification Search
CPC ..................................................... A61K 31/439
USPC ......................................................... 514/282
See application file for complete search history.

(56) References Cited

U.S. PATENT DOCUMENTS

| | | | |
|---|---|---|---|
| 2018/0148442 A1* | 5/2018 | Wang | C07D 471/04 |
| 2018/0344792 A1* | 12/2018 | Luo | A61P 11/06 |

OTHER PUBLICATIONS

A-Hong Chen, et al., "A new monoterpenoid indole alkaloid from *Ochrosia elliptica*", Journal of Natural Product Research, Taylor & Francis Online, vol. 31, Issue 13, 2017, pp. 1490-1494 (Abstract only).

Liang Feng, et al., "A Combination of Alkaloids and Triterpenes of *Alstonia scholaris* (Linn.) R. Br. Leaves Enhances Immunomodulatory Activity in C57BL/6 Mice and Induces Apoptosis in the A549 Cell Line", Molecules, vol. 18, No. 11, 2013, pp. 13920-13939.

Mei-Fen Bao, et al., "Cytotoxic Indole Alkaloids from *Tabernaemontana divaricata*", Journal of Natural Products, vol. 76, No. 8, 2013, pp. 1406-1412 (Abstract only).

J. Banerji, et al., "Constituents of Alstonia scholaris R.Br.—conversion of picrinine into strictamine and to a pyrrolidinoindolenine system", Indian Journal of Chemistry B, vol. 23B, No. 5, 1984, pp. 453-454 (Abstract only).

D. A. Evans, et al., "Alkaloids of *Rhazya orientalis*", Phytochemistry, vol. 7, Issue 8, Aug. 1968, pp. 1429-1431 (Abstract only).

* cited by examiner

*Primary Examiner* — Raymond J Henley, III
(74) *Attorney, Agent, or Firm* — Oblon, McClelland, Maier & Neustadt, L.L.P.

(57) ABSTRACT

A pharmaceutical composition containing an anticancer compound, named isopicrinine, isolated from the plant *Rhazya Stricta*. The pharmaceutical composition may contain a salt, an analog, a derivative, and/or the prodrug of isopicrinine. A method of treating cancer with the pharmaceutical composition is disclosed. A method of extracting isopicrinine is also disclosed.

17 Claims, 10 Drawing Sheets

Isopicrinine (A)          Picrinine (B)

PHARMACEUTICAL COMPOSITION FOR TREATING CANCER AND A METHOD THEREOF

BACKGROUND

Field of the Disclosure

This disclosure relates to a pharmaceutical composition containing a natural product with anticancer properties. A method of treating cancer with the pharmaceutical composition and a method of extracting the natural product are disclosed.

Description of the Related Art

Medicinal plants are a rich source of novel therapeutic drugs as the plants can produce bioactive molecules with diverse and complex structures which are still beyond the scope of current synthetic chemistry procedures.

Plant alkaloids are a diverse group of chemical compounds which contain a ring structure and nitrogen atoms. More than 27,683 alkaloids have been identified from various natural resources as mentioned in the dictionary of natural products. However, only 53 alkaloids have been developed successfully as drugs for therapeutic applications ranging from cough suppressants to anti-malarial agents. Vast majority of alkaloids from natural resources are yet to be explored and developed as potent drugs for treatment of various diseases in human. Alkaloids are known to have wide variety of pharmacological activities and have been used as therapeutics for treatment of various diseases. For example, quinine is used for treating malaria; ephedrine, theobromine, and theophylline are used for treating asthma; rescinnamine and reserpine are used for treating hypertension; and taxol, vinblastine, vincristine, and homoharringtonine are used for treating cancer.

Despite availability of several anticancer drugs in market, cancer still constitutes one of the major causes of death globally. It is therefore necessary to identify new and more potent anticancer drugs.

SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

A first aspect of the disclosure relates to a pharmaceutical composition comprising at least one of a compound represented by Formula (1), a derivative thereof, a solvate thereof, a salt thereof, a compound represented by Formula (2), a derivative thereof, a solvate thereof, and a salt thereof; and at least one exogenous pharmaceutically acceptable carrier and/or excipient which is not present in *Rhazya Stricta*, wherein Formula (1) and Formula (2) are:

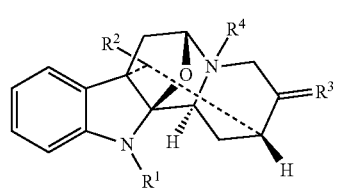
(1)

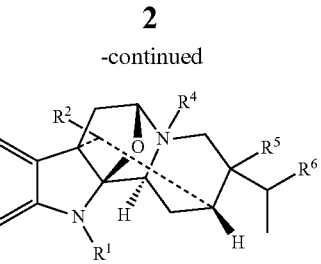
(2)

where $R^1$ is a hydrogen, an optionally substituted alkyl group, an optionally substituted cycloalkyl, an optionally substituted arylalkyl group, an optionally substituted alkanoyl, an optionally substituted aroyl, an optionally substituted alkylsulfonyl, or an optionally substituted arylsulfonyl;

$R^2$ is a carboxy group, a carboxylate group, an optionally substituted alkanoyloxy, an optionally substituted aroyloxy, or an optionally substituted carbamyl;

$R^3$ is O or an optionally substituted $CH_2$;

$R^4$ is a pair of electrons, a hydrogen, an optionally substituted alkyl group, an optionally substituted cycloalkyl, or an optionally substituted arylalkyl group, with the proviso when $R^4$ is an optionally substituted alkyl group, an optionally substituted cycloalkyl, or an optionally substituted arylalkyl group, the nitrogen atom attached to $R^4$ has a positive charge; and $R^5$ and $R^6$ are independently a hydrogen, a halogen, or a hydroxy.

In one embodiment, $R^1$ is a hydrogen.
In one embodiment, $R^2$ is $-CO_2CH_3$.
In one embodiment, $R^4$ is a pair of electrons.
In one embodiment, the compound represented by Formula (1) is:

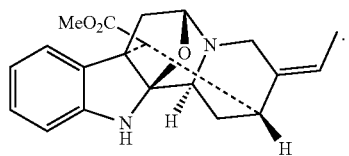 [SMILES: C/C=C1\CN2[C@H]3C[C@@H]1[C@@H](C(=O)OC)[C@]14C[C@H]2O[C@]31Nc1ccccc14]

In one embodiment, the pharmaceutical composition contains 0.0120 wt % of the compound represented by Formula (1) or Formula (2), based on a total weight of the pharmaceutical composition.

In one embodiment, the pharmaceutical composition contains 0.1-5 wt % of the compound represented by Formula (1) or Formula (2), based on a total weight of the pharmaceutical composition.

In one embodiment, the at least one exogenous pharmaceutically acceptable carrier and/or excipient is selected from the group consisting of an organic solvent, a synthetic polymer, a synthetic fatty ester, a fatty acid, a vegetable oil, and a surfactant.

In one embodiment, the at least one exogenous pharmaceutically acceptable carrier and/or excipient is an organic solvent selected from the group consisting of an alcohol, an alkyl methyl sulfoxide, an organic acid, a ketone, an ester, a lactam, and an amide.

In one embodiment, the at least one exogenous pharmaceutically acceptable carrier and/or excipient is a synthetic polymer selected from the group consisting of a polylactide, a polyglycolide, a polycaprolactone, a polyanhydride, a polyurethane, a polyesteramide, a polyorthoester, a polydioxanone, a polyacetal, a polyketal, a polycarbonate, a polyorthocarbonate, a polyphosphazene, a polyhydroxybutyrate, a polyhydroxyvalerate, a polyalkylene oxalate, a polyalkylene succinate, a poly(malic acid), poly(maleic anhydride), a polyvinyl alcohol, a copolymer thereof, a terpolymer thereof, or combinations thereof.

In one embodiment, the at least one exogenous pharmaceutically acceptable carrier and/or excipient is a fatty acid selected from the group consisting of an omega-3 fatty acid and an omega-6 fatty acid.

In one embodiment, the at least one exogenous pharmaceutically acceptable carrier and/or excipient is at least one vegetable oil selected from the group consisting of avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

A second aspect of the disclosure relates to a method of treating cancer in a subject in need thereof, the method comprising administering an effective amount of a compound of Formula (1) or Formula (2), a derivative thereof, a solvate thereof, or a combination thereof to the subject, wherein Formula (1) and Formula (2) are:

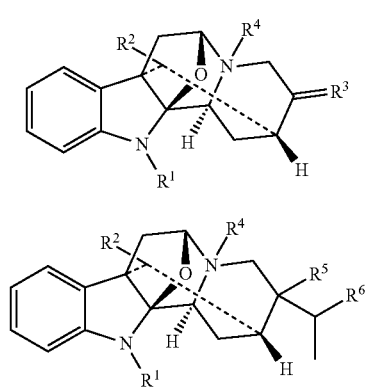

where $R^1$ is a hydrogen, an optionally substituted alkyl group, an optionally substituted cycloalkyl, an optionally substituted arylalkyl group, an optionally substituted alkanoyl, an optionally substituted aroyl, an optionally substituted alkylsulfonyl, or an optionally substituted arylsulfonyl;

$R^2$ is a carboxy group, an optionally substituted alkanoyloxy, an optionally substituted aroyloxy, or an optionally substituted carbamyl;

$R^3$ is O or an optionally substituted $CH_2$;

$R^4$ is a pair of electrons, a hydrogen, an optionally substituted alkyl group, an optionally substituted cycloalkyl, or an optionally substituted arylalkyl group, with the proviso when $R^4$ is an optionally substituted alkyl group, an optionally substituted cycloalkyl, or an optionally substituted arylalkyl group, the nitrogen atom attached to $R^4$ has a positive charge; and $R^5$ and $R^6$ are independently a hydrogen, a halogen, or a hydroxy.

In one embodiment, the cancer is at least one selected from the group consisting of lung cancer, stomach cancer, colon cancer, liver cancer, ovarian cancer, kidney cancer, breast cancer, prostate cancer, uterus cancer, melanoma, esophageal cancer, brain cancer, and pancreatic cancer.

In one embodiment, the cancer is breast cancer and/or pancreatic cancer.

In one embodiment, the effective amount of the compound of Formula (1) or Formula (2), a derivative thereof, a solvate thereof, or a combination thereof is in a range of 1-100 mg/kg body weight of the subject.

A third aspect of the disclosure relates to a method of extracting a compound from *Rhazya Stricta*, the method comprising: (i) mixing at least a first part of *Rhazya Stricta* or a first extract of *Rhazya Stricta* with a solution comprising water and an acid thereby forming a second extract; (ii) mixing the second extract with an organic solvent thereby forming a first aqueous layer and a first organic layer; (iii) mixing the first aqueous layer with a base thereby forming a neutralized aqueous layer; (iv) mixing the neutralized aqueous layer with the organic solvent thereby foil ing a second aqueous layer and a second organic layer; (v) concentrating the second organic layer thereby forming a residue comprising the compound; and (vi) isolating the compound, which is:

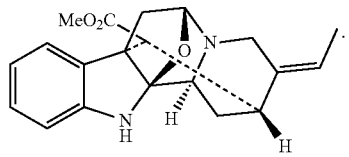 [SMILES: C/C=C1\CN2[C@H]3C[C@@H]1[C@@H](C(=O)OC)[C@]14C[C@H]2O[C@]31Nc1ccccc14]

In one embodiment, the acid is a mineral acid, the organic solvent is a chlorinated organic solvent, and the base comprises hydroxide.

In one embodiment, the first extract is obtained by mixing at least a second part of *Rhazya Stricta* with a plurality of organic solvents thereby forming the first extract. In one embodiment, the plurality of organic solvents comprises a chlorinated organic solvent and an alcohol.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
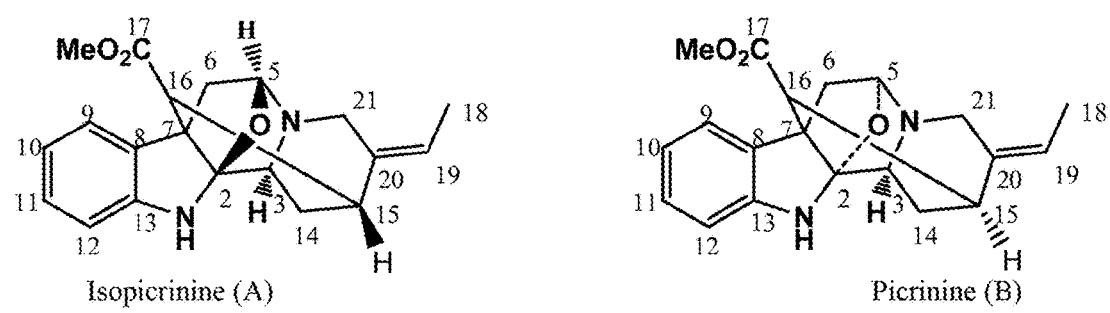
FIG. 1 shows the chemical structures of isopicrinine (A) isolated from *Rhazya stricta* and picrinine (B) isolated from *Alstonia scholaris*.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

Although the open-ended term "comprising," as a synonym of terms such as including, containing, or having, is use herein to describe and claim the present composition and methods, the composition and/or methods may alternatively be described using more limiting terms, such as "consisting of" or "consisting essentially of" the recited ingredients/steps. For example, a pharmaceutical composition which consists essentially of the recited ingredients may contain other ingredients which do not adversely affect the anticancer and/or therapeutic properties of the composition. Although various illustrative embodiments are described herein, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether.

The generally accepted convention for representing stereochemical compounds, which is also adhered to herein, is as follows:

the absence of stereo bonds may mean that the configuration of the stereogenic center(s) is not defined; and a compound represented with solid and broken wedges refers to a non-racemic or an enantio-enriched compound, where its stereochemistry is absolute.

*Rhazya stricta* is a native poisonous plant in Saudi Arabia, southern ran, Afghanistan, Pakistan, India, Iraq, Oman, and Yemen. The plant is an evergreen dwarf shrub of the Apocynaceae family. *Rhazya stricta* has been used traditionally for the treatment of various diseases in many Middle East and South Asian countries. *Rhazya stricta* is known to be a rich source of several potent compounds with novel structures and with wide variety of pharmaceutical applications for treatment of various diseases such as diabetes, inflammatory diseases, sore throat, helminthesis, arthritis, and cancer (Atta-ur-Rahman, Qureshi, M. M., Zaman, K., Malik, S., Ali, S. S. 1989. The alkaloids of *Rhazya stricta* and *R. orientalis*. A review. Fitoterapia 60: 291-322, incorporated herein by reference in its entirety). Several studies have revealed the potential of this plant as an important source of phytochemicals with anticancer properties. *Rhazya stricta* produces a large number of terpenoid indole alkaloids. More than 100 alkaloids with diverse structure and pharmacological properties have been purified and characterized from the leaves, root, stem and fruits of *Rhazya stricta*. However, till now, chemical structures of only 78 alkaloids from *Rhazya stricta* have been reported and the pharmacological action of very few alkaloids is defined (Marwat, S. K., Fazal-ur-Rehman, Usman, K., Shah, S. S., Anwar, N., Ullah, I. 2012. A review of phytochemistry, bioactivities and ethnomedicinal uses of *Rhazya stricta* Decsne. Afr. J. Microbiol. Res. 6(8): 1629-1641; and Obaid, A. Y., Voleti, S., Bora, R. S., Hajrah, N. H., Omer, A. M. S., Sabir, J. S. M., Saini, K. S. 2017. Cheminformatics studies to analyze the therapeutic potential of phytochemicals from *Rhazya stricta*. Chem. Cent. J. 11:11. DOI 10.1186/s13065-017-0240-1, each incorporated herein by reference in their entirety).

Some of the alkaloids isolated from *Rhazya stricta*, such as akuammidine, rhazimanine, stemmadenine, strictanol, and tetrahydrosecaminediol, have shown potential anti-microbial activity against various bacterial pathogens. These alkaloids, which are predominantly present in the leaves of the plants, have shown potent anti-bacterial activity against *Pseudomonas aeruginosa, Escherichia coli, Staphylococcus aureus* and *Candida albicans*.

Several studies have demonstrated the anticancer, antioxidant, and free radical scavenging properties of the phytochemicals present in *Rhazya Stricta*. Alkaloids such as sewarine, vallesiachotamine, tetrahydrosecamine, tetrahydro-secaminediol, and strictanol have been shown to possess anti-carcinogenic properties (Mukhopadhayay, S., Handy, G. A., Funayama, S., Cordell, G. A. 1981. Anticancer indole alkaloids of *Rhazya stricta*. J. Nat. Prod. 44:696-700; and Baeshen, M. N., Khan, R., Bora, R. S., Baeshen, N. A. 2015. Therapeutic potential of the folkloric medicinal plant *Rhazya stricta*. Biol. Syst. Open Access, 5:1, each incorporated herein by reference in their entirety). Rhazinilam has been shown to exert cytotoxic activity by inhibiting microtubule assembly and promoting the growth of abnormal tubulin spirals (Gu, Z., Zakarian, A. 2010. Total Synthesis of Rhazinilam: Axial to point chirality transfer in an enantiospecific Pd-catalyzed transannular cyclization. Org. Lett. 12: 4224-4227, incorporated herein by reference in its entirety).

While previous research efforts have focused on using leaf extracts or total alkaloids fraction to determine the anticancer potential of Rhazya stricta, there is utmost need to isolate and purify the individual alkaloid with anticancer activity to realize their potential as a new anticancer drug (Baeshen, N. A., Elkady, A. I., Abuzinadah, O. A., Mutwakil, M. H. 2012. Potential anticancer activity of the medicinal herb, Rhazya stricta, against human breast cancer. Afr. J. Biotechnol. 11(37): 8960-8972; and Elkady, A. I., Hussein, R. A. H., Abu-Zinadah, O. A. 2014. Differential control of growth, apoptotic activity and gene expression in human colon cancer cells by extracts derived from edicinal herbs Rhazya stricta and Zingibar officinale and their combination. World J. Gastroenterol. 20(41):15275-15288, each incorporated herein by reference in their entirety).

Further, there is a need to purify alkaloids from Rhazya stricta in a sufficient amount to analyze their anticancer potential and decipher their mechanism of action using differential gene expression studies with RNA-Seq or microarray technology.

An aspect of the disclosure relates to a method of extracting a compound represented by Formula (1) from Rhazya Stricta. The compound, isopicrinine, is a stereoisomer of picrinine and has not been reported before.

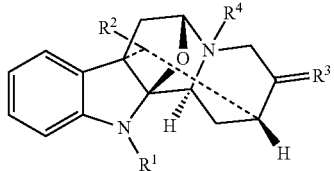
(1)

where $R^1$ is a hydrogen;
$R^2$ is —$CO_2CH_3$;
$R^3$ is =$CHCH_3$; and
$R^4$ is a pair of electrons.

Isopicrinine may be extracted from the whole plant, flowers, buds, seeds, leaves, fruits, pulp, twigs, stems, bark, roots, and combinations thereof. Preferably, isopicrinine is extracted from at least a part of a leaf. The Rhazya Stricta plant may be at any growth stage, e.g. at a flowering stage when the flower and/or one or more non-flower parts (e.g. leaf, stem, and root) may be used, or alternatively, at a non-flowering stage, when one or more non-flower parts may be used. The plant part(s) of interest may be collected and then washed thoroughly, preferably twice/thrice with rater, to remove both epiphytes and necrotic plants; preferably followed by washing with water to remove associated debris if any. In some embodiments, tap water, distilled water, doubly distilled water, deionized water, deionized distilled water, or combinations thereof may be used to wash the plant part(s) of interest. The water may be sterile. In one embodiment, the water may have a conductivity of less than 10 µS·cm-1, less than 5 µS·cm-1, or less than 1 µS·cm-1 at 20-30° C.; and/or a resistivity greater than 0.1 MΩ·cm, greater than 1 MΩ·cm, greater than 5 MΩ·cm, or greater than 10 MΩ·cm at 20-30° C.; and/or a total solid concentration less than 5 mg/kg, less than 1 mg/kg, or less than 0.5 mg/kg; and/or a total organic carbon concentration less than 1000 µg/L, less than 200 µg/L, or less than 50 µg/L. The clean and fresh plant part(s) may be sun-dried or dried in the shade/dark room for 5-25 days, or preferably 7-20 days, or more preferably 10-15 days, and then finely cut/chopped, or preferably ground/powdered/pulverized using, for example, a domestic blender.

The first extract of Rhazya Stricta may be obtained by expression, fermentation, distillation, steam distillation, pressing, organic extraction, supercritical $CO_2$ extraction, or additional extraction methods known to those familiar in the art. For example, the first extract may be obtained by extracting fresh/dried/ground plant part(s) of interest with supercritical $CO_2$ at a pressure of 140-300 bar, 180-250 bar, or 200-220 bar, at 50-80° C., or 55-70° C., for 30-240 minutes, 60-180 minutes, or 100-150 minutes. In another embodiment, the first extract of Rhazya Stricta is obtained by mixing the fresh/dried/ground plant part(s) of interest with a plurality of organic solvents.

Exemplary organic solvents include ethers (e.g. diethyl ether, dibutyl ether, tetrahydrofuran, 1,4-dioxane, tetrahydropyran, t-butyl methyl ether, cyclopentyl methyl ether, di-iso-propyl ether), alcohols (e.g., methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), polyols (propylene glycol, polyethylene glycol, glycerol, poly(tetramethylene ether) glycol), aromatic solvents (e.g. benzene, o-xylene, m-xylene, p-xylene, and mixtures of xylenes, toluene, mesitylene, anisole, 1,2-dimethoxybenzene, α,α,α,-trifluoromethylbenzene, fluorobenzene), hydrocarbons (e.g., cyclohexane, hexane, isooctane, n-pentane), and chlorinated solvents (dichloromethane, chloroform, carbon tetrachloride, perchloroethylene (tetrachloroethylene), 1,1,2,2-tetrachloroethane, 1,1,2-trichloroethane, trichloroethylene, methyl chloroform (1,1,1-trichloroethane), 1,2,3-trichloropropane, ethylene dichloride, 1,2-dichloropropane (propylene dichloride), 1,2-dichloroethylene, 1,1-dichloroethane, chlorobenzene).

Preferably, the plurality of organic solvents comprises a chlorinated organic solvent (e.g., chloroform) and an alcohol (e.g., ethanol). A volume ratio between the chlorinated organic solvent and the alcohol may range from 2:1 to 1:10, 1:1 to 1:7, or 1:2 to 1:5. This solvent pair may result in a higher extracted yield of isopicrinine.

An amount of the fresh/dried/ground plant part(s) may be 0.01-5 g/ml, 0.05-3 g/ml, 0.1-2 g/ml or 0.2-1 g/ml of the plurality of the organic solvents. The fresh/dried/ground plant part(s) of interest may be soaked in the plurality of organic solvents for longer than 1 hour, 5 hours, or 10 hours, and up to 5 days, 4 days, or 3 days. The resulting mixture may be agitated for at least a part of the soaking duration by an agitator, a vortexer, a rotary shaker, a magnetic stirrer, a centrifugal mixer, or an overhead stirrer. In another embodiment, the resulting mixture is left to stand (i.e. not stirred). In one embodiment, the resulting mixture is sonicated in an ultrasonic bath or with an ultrasonic probe. The soaking may occur at a temperature in a range of 16-32° C., 20-30° C., or 24-28° C. Alternatively, the resulting mixture may be heated at a temperature of 40-70° C., 45-60° C., or 50-55° C. for at least a part of the soaking duration. An external heat source, such as a water bath or an oil bath, an oven, microwave, or a heating mantle, may be employed to heat the mixture. In a preferred embodiment, the external heat source is a thermostatted thermocirculator. After the heating, the resulting mixture may be filtered until no insoluble material appears in the filtrate. The process of extraction may be carried out for up to six times, four times, or three times. For example, the residue collected from the filtration may be mixed with fresh organic solvents for subsequent rounds of extraction. The filtrate (or combined filtrate from several rounds of extraction) may be concentrated under a reduced pressure thereby obtaining the first extract.

In some embodiments, the first extract or fresh/dried/ground plant part(s) of interest may be mixed with a solution comprising water and an acid thereby forming a second extract. For example, fresh/dried/ground plant part(s) of interest may be soaked in the solution for longer than 1 hour, 5 hours, or 10 hours, and up to 5 days, 4 days, or 3 days. An amount of the fresh/dried/ground plant part(s) may be 0.01-5 g/ml, 0.05-3 g/ml, 0.1-2 g/ml or 0.2-1 g/ml of solution. The resulting mixture may be agitated using the methods disclosed herein or left to stand. The resulting mixture may be heated at a temperature of 60-100° C., 70-90° C., or 75-85° C. for at least a part of the soaking duration with the methods disclosed herein. After the heating, the resulting mixture may be filtered until no insoluble material appears in the second extract. In some embodiments, the hot water percolation method is used.

The acid may be an organic acid (e.g., acetic acid, formic acid, propionic acid, butyric acid, pentanoic acid, hexanoic acid, oxalic acid, lactic acid, malic acid, citric acid, benzoic acid, p-toluenesulfonic acid, trifluoromethanesulfonic acid, aminomethylphosphonic acid); a mineral acid (e.g., hydrochloric acid, nitric acid, phosphoric acid, sulfuric acid, hydrobromic acid, perchloric acid, hydroiodic acid); or mixtures thereof. Preferably, the acid is a non-oxidizing mineral acid, such as hydrochloric acid, to minimize the oxidation of the alkaloids. An amount of the acid in the solution may be 0.5-10 wt %, 1-7 wt %, or 2-5 wt %, based on a total weight of the solution.

The second extract may be mixed with an organic solvent using the agitation methods disclosed herein or by shaking a separatory funnel containing the second extract and the organic solvent. A volume ratio of the second extract to the organic solvent may be in a range of 20:1 to 1:20, 10:1 to 1:10, 7:1 to 1:7, 4:1 to 1:4, or 2:1 to 1:2. The organic solvent of the disclosed method may be any of the organic solvent disclosed herein. Preferably, the organic solvent used for extracting isopicrinine from the second extract has a low solubility in water, and a capability of extracting the isopicrinine from the second extract. Preferably, the organic solvent is a chlorinated solvent, such as chloroform, to facilitate the removal of the organic layer.

After mixing the second extract with the organic solvent, the resulting mixture is allowed to stand for a sufficient period of time, e.g. at least 30 seconds, at least 1 minute, at least 3 minutes, at least 5 minutes, etc., for the complete formation of the first organic layer and the first aqueous layer. In another embodiment, the resulting mixture may be centrifuged for an effective period of time (e.g. at least 1 minute, at least 3 minutes, or at least 5 minutes, etc.), at an effective speed (e.g. 1000-6000 rpm, at 3000-5000 rpm, or at 4000 rpm).

The first aqueous layer may be mixed with a base thereby forming a neutralized aqueous layer with a pH of 6.8 to 7.2. Exemplary bases include, without limitation, an inorganic base, such as an alkali metal hydroxide (e.g. lithium hydroxide, potassium hydroxide, sodium hydroxide, cesium hydroxide), an alkali metal bicarbonate (e.g. lithium bicarbonate, potassium bicarbonate, sodium bicarbonate, cesium bicarbonate), an alkali metal carbonate (e.g. lithium carbonate, potassium carbonate, sodium carbonate, cesium carbonate), an alkaline earth metal carbonate (e.g. magnesium carbonate, calcium carbonate, strontium carbonate, radium carbonate), trialkylammonium hydroxide (e.g., tetrakis(decyl)ammonium hydroxide, tetrabutylammonium hydroxide, benzyltrimethylammonium hydroxide, tetraethylammonium hydroxide), an alkali metal acetate (e.g. lithium acetate, sodium acetate, potassium acetate); and an organic base such as an amine, for example, a trialkylamine (e.g., trimethylamine, tri-n-butylamine) of formula $NR'_3$ (where each R' may be independently methyl, ethyl, n-propyl, and n-butyl), a dialkylamine of formula $HNR'_2$ (e.g., diethylamine, di-n-butylamine, diisopropylethylamine, dicyclohexylmethylamine), pyrrolidine, piperidine, pyridine, 2,6-dimethylpyridine, 4-aminopyridine, N-methyl-2,2,6,6-tetramethylpiperidine, 2,2,6,6-tetramethylpiperidine, 2,6-di-tert-butylpyridine, 1,4-diazabicyclo[2.2.2]octane), and mixtures thereof. In preferred embodiments, the base is ammonium hydroxide.

The neutralized aqueous layer may be mixed with the same or different organic solvent using the agitation methods disclosed herein. The resulting mixture may be centrifuged or allowed to stand thereby forming a second aqueous layer and a second organic layer.

The second organic layer and the first organic layer may be combined and then concentrated by boiling away the solvent or removing the solvent under reduced pressure (e.g., 10-500 mbar, 50-300 mbar, or 100-200 mbar). A residue comprising isopicrinine remains after the solvent is removed.

Isopicrinine may be isolated and purified by methods known to those skilled in the art such as distillation, crystallization, column chromatography, and high pressure liquid chromatography (HPLC) (normal phase or reversed phase). Preferred methods include, purifying the residue with column chromatography (with silica or alumina as the stationary phase), preparative thin layer chromatography, and recrystallization. In one embodiment, the residue is purified with an alumina column. A weight ratio of the residue to the alumina may be in a range of 1:20 to 1:80, 1:30 to 1:60, or 1:40 to 1:50. Isocratic or gradient elution may be used. A single organic solvent or a mixture of organic solvents may be used to elute isopicrinine. For example, chloroform only, chloroform/ethyl acetate, and/or chloroform/methanol may be used in succession. In a preferred embodiment, isopicrinine is eluted with a mixture of chloroform and ethyl acetate in a volume ratio of (chloroform:ethyl acetate) 7.5:2.5 to 9:1, 8:2 to 8.5 to 1.5, or about 8.5:1.5. Isopicrinine may be further purified with preparative thin layer chromatography (alumina stationary phase) using a mixture of chloroform and methanol in a volume ratio of (chloroform:methanol) 8:2 to 9.9:0.1, 8.5:1.5 to 9.5:0.5, or about 9.5:0.5. The retention factor ($R_f$) of isopicrinine may be 0.45-0.5, 0.46-0.49, or 0.47-0.48.

Another aspect of this disclosure relates to a method of making derivatives of isopicrinine. The nitrogen atoms, the ester group, and the alkene group may undergo reactions as described hereinafter. The progress of the reactions may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy. The reaction product(s) may be isolated and purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase.

Alkylating Isopicrinine

Each nitrogen atom in isopicrinine may be independently alkylated by reacting with a compound represented by formulae $R^1X$ or $R^4X$, where $R^1$ and $R^4$ are each independently an optionally substituted alkyl group, an optionally substituted cycloalkyl group, or an optionally substituted arylalkyl group, and X is a leaving group such as Cl, Br, I, OTf (triflate), OTs (tosylate), or mesylate. Exemplary $R^1X$ and $R^4X$ include, without limitation, methyl bromide, methyl iodide, ethyl bromide, ethyl iodide, propyl bromide, propyl iodide, (bromomethyl)cyclohexane, (iodomethyl)cyclohexane, 1-chloro-2,5-dimethylhexane, 1-bromo-2,5-dimethylhexane, 1-iodo-2,5-dimethylhexane, 1-chloro-3-methylcyclobutane, 1-bromo-3-methylcyclobutane, 1-iodo-3-methylcyclobutane, benzyl bromide, benzyl iodide, benzyl tosylate, and benzyl mesylate.

The isopicrinine may be mixed with an inorganic base in a polar aprotic solvent. Preferably, the inorganic base is potassium carbonate and the polar aprotic solvent is dimethyl formamide. The mixture may be left to stand or agitated with the methods disclosed herein at 16-32° C., 20-30° C., or 24-28° C. The mixture may be heated to 40-100° C., 50-90° C., or 60-80° C. using the methods disclosed herein. $R^1X$ or $R^4X$ may be mixed with the same solvent, and the resulting RX or $R^4X$ solution may be mixed with or added to the mixture containing isopicrinine at a rate of 0.1-2 ml/s, 0.5-1.7 ml/s, 0.8-1.5 ml/s. A concentration of isopicrinine in the resulting reaction mixture may be 0.1-1 M, 0.3-0.8 M, 0.4-0.6 M. A concentration of the inorganic base in the resulting reaction mixture may be 0.05-1 M, 0.1-0.6 M, 0.2-0.4 M. A concentration of the $R^1X$ or $R^4X$ in the resulting reaction mixture may be 0.01-1 M, 0.05-0.5 M, 0.1-0.4 M. A mole ratio of the $R^1X$ or $R^4X$ to the natural compound may range from 10:1 to 1:1, 6:1 to 2:1, or 5:1 to 3:1. A mole ratio of $R^1X$ or $R^4X$ to the inorganic base may range from 5:1 to 1:1, 4:1 to 1:1, or 3:1 to 1:1. The reaction mixture may be left to stand or agitated with the methods disclosed herein at 16-32° C., 20-30° C., or 24-28° C., or heated to 40-100° C., 50-90° C., or 60-80° C. using the methods disclosed herein. The reaction mixture may be agitated for 1-10 hours, 3-8 hours, or 4-6 hours thereby forming alkylated isopicrinine.

Amidating/Sulfonating Isopicrinine

The nitrogen atom of the secondary amine may be amidated or sulfonated by reacting isopicrinine with an acyl halide (i.e., an optionally substituted alkanoyl halide or an optionally substituted aroyl halide) or a sulfonyl halide (i.e., an optionally substituted alkylsulfonyl halide or an optionally substituted arylsulfonyl halide). The acyl halide and the sulfonyl halide may be represented by the formula $R^1Y$, where $R^1$ is an optionally substituted alkanoyl, an optionally substituted aroyl, an optionally substituted alkylsulfonyl, or an optionally substituted arylsulfonyl, and Y can be Cl, Br, or I. Examples of acyl halide and sulfonyl halide include, without limitation, acetyl chloride, acetyl bromide, acetyl iodide, acryloyl chloride, acryloyl bromide, acryloyl iodide, anisoyl chloride, anisoyl bromide, anisoyl iodide, benzoyl chloride, benzoyl bromide, benzoyl iodide, butyryl chloride, butyryl bromide, butyryl iodide, methanesulfonyl chloride, methanesulfonyl bromide, methanesulfonyl iodide, ethanesulfonyl chloride, ethanesulfonyl bromide, ethanesulfonyl iodide, 4-hexylbenzene-1-sulfonyl chloride, 1,4-benzodioxan-6-sulfonyl chloride, biphenyl-4-sulfonyl chloride, 4'-chlorobiphenyl-4-sulfonyl chloride, 4'-methoxybiphenyl-4-sulfonyl chloride, 4'-fluorobiphenyl-4-sulfonyl chloride, 4'-methylbiphenyl-4-sulfonyl chloride, 2-chlorobenzylsulfonyl chloride, 4-chlorobenzylsulfonyl chloride, cyclopentanesulfonyl chloride, cyclopropanesulfonyl chloride, 3,4-dichlorobenzylsulfonyl chloride, 4-methylbenzylsulfonyl chloride, 2,4,5-trichlorobenzenesulfonyl chloride, and 3,3,3-trifluoropropane-1-sulfonyl chloride.

Isopicrinine may be mixed with acyl halide or the sulfonyl halide in the presence of an aprotic solvent and an organic base. Preferably, the aprotic organic solvent is dichloromethane, acetonitrile, or toluene, and/or the organic base is pyridine. Concentrations of isopicrinine, acyl halide, or the sulfonyl halide, and the organic base in the reaction mixture may independently range from 0.1-1 M, 0.2-0.8 M, 0.3-0.5 M. A mole ratio of isopicrinine to $R^1Y$ may range from 1:1 to 1:2, 1:1.01 to 1:1.3, or 1:1.02 to 1:1.1. A mole ratio of isopicrinine to the organic base may range from 1:1 to 1:2, 1:1.05 to 1:1.3, or 1:1.1 to 1:1.2. The reaction mixture may be left to stand or agitated with the methods disclosed herein at 16-32° C., 20-30° C., or 24-28° C., or heated to 40-100° C., 50-90° C., or 60-80° C. using the methods disclosed herein. The reaction mixture may be agitated for 1-30 hours, 5-20 hours, or 15-18 hours thereby forming the amidated or sulfonated isopicrinine.

Hydrolysis of the Methyl Ester

The ester group ($—CO_2CH_3$) may be hydrolyzed with acids or bases to form the carboxy group ($—COOH$) or the carboxylate group ($—COO^-$), respectively. For example, isopicrinine may be mixed with a mineral acid or an inorganic base in a protic solvent. Preferably, the protic solvent is water, methanol, or combinations thereof. The concentration of isopicrinine may range from 0.1-1 M, 0.2-0.8 M, 0.3-0.5 M. The mineral acid or the inorganic base is present in an amount ranging from 1-40 mol %, 5-30 mol %, or 10-20 mol %, based on the number of moles of isopicrinine. The reaction mixture may be left to stand or agitated with the methods disclosed herein at 16-32° C., 20-30° C., or 24-28° C., or heated to 40-100° C., 50-90° C., or 60-80° C. using the methods disclosed herein. The reaction mixture may be agitated for 1-30 hours, 5-20 hours, or 15-18 hours thereby hydrolyzing the methyl ester.

Transesterification of Methyl Ester

The ester group ($—CO_2CH_3$) may undergo a transesterification reaction with an alcohol which is not methanol. For example, isopicrinine may be mixed with an optionally substituted alkyl alcohol, or an optionally substituted aryl alcohol in the presence of a mineral acid and optionally a polar aprotic solvent. Exemplary alcohols include those described above and an optionally substituted phenol (e.g., phenol, catechol, hydroquinone, 2,6-dimethoxybenzoquinone, gallic acid, and salicylic acid). Preferably, the mineral acid is hydrochloric acid and/or the solvent (if present) is THF. The concentrations of isopicrinine and the alcohol may independently range from 0.1-1 M, 0.2-0.8 M, 0.3-0.5 M. An amount of the mineral acid may range from 1-20 mol %, 5-15 mol %, or 8-12 mol %, based on a number of moles of isopicrinine. The reaction mixture may be left to stand or agitated with the methods disclosed herein at 16-32° C., 20-30° C., or 24-28° C., or heated to 40-100° C., 50-90° C., or 60-80° C. using the methods disclosed herein. The reaction mixture may be agitated for 1-30 hours, 5-20 hours, or 15-18 hours thereby forming the reaction product.

Alternatively, transesterification can be accomplished in two steps. The first step is a hydrolysis of the methyl ester as described above or by methods known to those skilled in the art. The second step is an esterification of the carboxy/carboxylate group and the esterification method is known to those in the art.

Transamidation of Methyl Ester

The ester group (—$CO_2CH_3$) may undergo a transamidation reaction with an optionally substituted amine. For example, isopicrinine may be mixed with an optionally substituted amine in the presence of a tert-butoxide and a polar protic solvent. Exemplary amines include those described above and primary amines (e.g., methylamine, ethylamine, propylamine, cyclobutylamine, cyclopentylamine). Exemplary tert-butoxide includes, without limitation, potassium tert-butoxide, lithium tert-butoxide, sodium tert-butoxide, magnesium tert-butoxide, and barium tert-butoxide. The polar protic solvent is preferably water. In some embodiments, a polar aprotic solvent (e.g., THF) is present in addition to water. Concentrations of isopicrinine, the optionally substituted amine, and the tert-butoxide in the reaction mixture may independently range from 0.1-1 M, 0.2-0.8 M, 0.3-0.5 M. A mole ratio of isopicrinine to the optionally substituted amine may range from 1:1 to 1:2, 1:1.01 to 1:1.3, or 1:1.02 to 1:1.1. A mole ratio of isopicrinine to the tert-butoxide may range from 1:1 to 1:5, 1:1.5 to 1:3, or about 1:2. The reaction mixture may be left to stand or agitated with the methods disclosed herein at 16-32° C., 20-30° C., or 24-28° C., or heated to 40-65° C., 45-60° C., or 50-55° C. using the methods disclosed herein. The reaction mixture may be agitated for 5-120 minutes, 10-100 minutes, or 30-60 minutes thereby forming the reaction product.

Alternatively, transamidation can be accomplished in two steps. The first step is a hydrolysis of the methyl ester as described above or by methods known to those skilled in the art. The second step is an amide bond formation between the carboxy/carboxylate group and the amine using methods known to those in the art.

Reactions of the Alkene

The alkene moiety may undergo several reactions such as ozonolysis, hydrogenation, hydroxylation, dihydroxylation, epoxidation, halogenation, and other addition reactions with HCl, HBr, and HI. Examples of the reaction procedures are described hereinafter.

Ozonolysis of Alkene

Isopicrinine may be dissolved in an aprotic organic solvent such as dichloromethane and acetone. The organic solvent may contain water in an amount up to 10 vol %, 7 vol %, or 5 vol %, based on a total volume of the organic solvent. A concentration of isopicrinine may be 0.1-1 M, 0.2-0.8 M, 0.3-0.5 M. Ozone may be bubbled into the solution containing isopicrinine. Preferably, the reaction mixture is agitated by the methods disclosed herein such as using a magnetic stirrer. The reaction mixture may be agitated at −5° C. to 5° C., −3° C. to 3° C., or −1° C. to 1° C. for 1-10 hours, 2-7 hours, or 4-6 hours. The reaction mixture may be temperature-regulated to prevent overheating and/or evaporation, for example, by a thermostatted circulator, a water and/or ice bath with/without salt, or ice packs. After the agitation, dimethyl sulfide may be added to the reaction mixture thereby forming the isopicrinine ketone.

Hydrogenation of Alkene

Isopicrinine may be dissolved in an aprotic solvent (preferably ethyl acetate) thereby forming a solution with a concentration of isopicrinine in a range of 0.1-1 M, 0.2-0.8 M, 0.3-0.5 M. A catalyst (e.g., palladium on carbon) may be added to the solution in an amount of 1-30 wt %, 5-20 wt %, or 8-15 wt %, based on the weight of the isopicrinine. Hydrogen gas may be bubbled into the reaction mixture. Alternatively, the reaction flask may be pressurized with hydrogen gas to a pressure of 2-10 bar, 3-8 bar, or 4-6 bar. Preferably, the reaction mixture is agitated by the methods disclosed herein or with a shaker hydrogenation apparatus for 0.5-30 hours, 4-20 hours, or 8-15 hours thereby forming hydrogenated isopicrinine.

Halogenation of Alkene

Isopicrinine may be mixed with halogens, such as chlorine ($Cl_2$), bromine ($Br_2$), and iodine ($I_2$), in the presence of a chlorinated solvent (e.g., chloroform). A concentration of isopicrinine may be 0.1-1 M, 0.2-0.8 M, 0.3-0.5 M. A concentration of bromine or iodine in the reaction mixture may be 0.2-10 M, 0.4-8 M, 0.6-6 M. A mole ratio of isopicrinine to the bromine or iodine may be 1:2 to 1:10, 1:3 to 1:8, or 1:5 to 1:7. For the chlorination reaction, chlorine gas is bubbled into the reaction mixture. The reaction mixture may be agitated at 16-32° C., 20-30° C., or 24-28° C. and irradiated with a light source such as a xenon lamp, a mercurial lamp, a metal halide lamp, a LED lamp, a LED chip, a solar simulator, and a halogen lamp. Two or more light sources may be used. Sunlight may also be used as the light source. The irradiation source may be fitted with a filter to block or attenuate light with wavelengths longer than 400 nm. In some embodiments, the irradiation source is a flame, a lantern, a gas discharge lamp, an incandescent bulb, a laser, a fluorescent lamp, an electric arc, a cathode ray tube. Preferably the irradiation source may have a total power output of 50-1,000 W, preferably 100-750 W, more preferably 250-600 W, and may be positioned 5-30 cm, preferably 7-20 cm, more preferably 8-15 cm from the closest surface of the mixture. The mixture may be irradiated for at least 1 minute, at least 10 minutes, or at least 20 minutes, and not more than 600 minutes, not more than 300 minutes, or not more than 100 minutes. Alternatively, the reaction mixture may be heated to 40-60° C., 45-55° C., or 48-52° C. using the methods disclosed herein thereby forming halogenated isopicrinine.

Hydroxylation of Alkene

Isopicrinine may be mixed with borane complexed with THF (borane-THF) in the presence of a dried aprotic solvent such as THF. The mixture may be left to stand or agitated at −5° C. to 5° C., −3° C. to 3° C., or −1° C. to 1° C. for 1-10 hours, 2-7 hours, or 4-6 hours. The mixture may be temperature-regulated to prevent overheating and/or evaporation using the methods described above. After which, a solution containing an inorganic base (e.g., sodium hydroxide) and a solution containing hydrogen peroxide may be added to the mixture. In the resulting reaction mixture, concentrations of isopicrinine and borane-THF may independently be 0.1-1 M, 0.2-0.8 M, 0.3-0.5 M. A concentration of the solution containing the inorganic base may range from 0.5-5 M, 1-4 M, or 2-3 M. A concentration of the hydrogen peroxide solution may be 10-50 wt %, 20-40 wt %, or 25-35 wt %, based on a total weight of the hydrogen peroxide solution. A mole ratio of isopicrinine to borane.THF may be 1:1 to 1:2, 1:1.01 to 1:1.3, or 1:1.02 to 1:1.1. A mole ratio of the solution containing the inorganic base to isopicrinine may be 1:1 to 1:3, 1:1.01 to 1:1.5, or 1:1.02 to 1:1.2. A mole ratio of the solution containing hydrogen peroxide to isopicrinine may be 1:1 to 1:4, 1:1.01 to 1:2, or 1:1.02 to 1:1.5. The reaction mixture is heated to 40-70° C., 45-65° C., or 50-60° C. for 10-120 minutes, 30-100 minutes, or 40-60 minutes thereby forming the reaction product.

Dihydroxylation of Alkene

Isopicrinine may be mixed with hydrogen peroxide, and a catalyst, such as osmium tetroxide, vanadium oxide, or chromium oxide, in a solvent. The solvent may contain an alcohol, such as tert-butanol, and water. A concentration of isopicrinine may be 0.1-5 M, 0.5-4 M, 2-3 M. A concentration of hydrogen peroxide in the reaction mixture may be 0.1-15 M, 0.5-12 M, 2-9 M. A mole ratio of the isopicrinine to hydrogen peroxide may range from 1:1 to 1:3, 1:1.1 to 1:2, or about 1:1.5. An amount of the catalyst may be 0.1-1 mol %, 0.2-0.7 mol %, or 0.3-0.5 mol % of the number of moles of the isopicrinine. The resulting reaction mixture is then stirred at −5° C. to 5° C., −3° C. to 3° C., or −1° C. to 1° C. for 5-60 hours, 10-50 hours, or 30-40 hours thereby forming dihydroxylated isopicrinine. The reaction mixture may be temperature-regulated to prevent overheating and/or evaporation, for example, by a thermostatted circulator, a water and/or ice bath with/without salt, or ice packs.

Allylic Oxidation

Isopicrinine may be mixed with selenium dioxide in an alcohol such as t-butanol. Hydrogen peroxide solution may be added at a rate of 0.05-0.5 ml/min, 0.1-0.4 ml/min, or 0.2-0.3 ml/min to the mixture containing isopicrinine. A concentration of the hydrogen peroxide solution may be 3-50 wt %, 10-40 wt %, or 20-30 wt %, based on a total weight of the solution. A mole ratio of the isopicrinine to hydrogen peroxide may range from 1:1 to 1:3, 1:1.1 to 1:2, or about 1:1.3 to 1:1.5. An amount of the selenium dioxide is in a range of 0.1-1 mol %, 0.2-0.7 mol %, or 0.3-0.5 mol % of the number of moles of the isopicrinine. A concentration of isopicrinine may range from 0.5-5 M, 1-4.5 M, or 3-4 M. The reaction mixture may be heated to 35-70° C., 40-65° C., or 45-50° C. for 10-240 minutes, 30-180 minutes, or 40-120 minutes thereby forming the allylic alcohol.

Another aspect of the disclosure relates to a pharmaceutical composition comprising or consisting essentially of at least one of a compound represented by Formula (1), a derivative thereof, a solvate thereof, a salt thereof, a compound represented by Formula (2), a derivative thereof, a solvate thereof, and a salt thereof; and at least one exogenous pharmaceutically acceptable carrier and/or excipient which is not present in *Rhazya Stricta*.

Formula (1) and Formula (2) are:

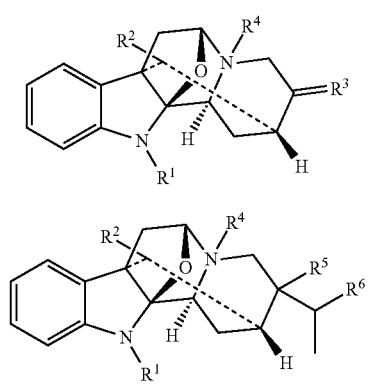

where $R^1$ is a hydrogen, an optionally substituted alkyl group, an optionally substituted cycloalkyl, an optionally substituted arylalkyl group, an optionally substituted alkanoyl, an optionally substituted aroyl, an optionally substituted alkylsulfonyl, or an optionally substituted arylsulfonyl;

$R^2$ is a carboxy group, an optionally substituted alkanoyloxy, an optionally substituted aroyloxy, or an optionally substituted carbamyl;

$R^3$ is O or an optionally substituted $CH_2$;

$R^4$ is a pair of electrons, a hydrogen, an optionally substituted alkyl group, an optionally substituted cycloalkyl, or an optionally substituted arylalkyl group, with the proviso when $R^4$ is an optionally substituted alkyl group, an optionally substituted cycloalkyl, or an optionally substituted arylalkyl group, the nitrogen atom attached to $R^4$ has a positive charge; and $R^5$ and $R^6$ are independently a hydrogen, a halogen, or a hydroxy.

The term "alkyl", as used herein, unless otherwise specified, refers to a straight, branched, or cyclic hydrocarbon fragment. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl. As used herein, the term "cyclic hydrocarbon" refers to a cyclized alkyl group. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as exemplary 1-methylcyclopropyl and 2-methycyclopropyl groups, are included in the definition of cycloalkyl as used in the present disclosure.

The term "aryl", as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, stearoyl.

The term "aroyl" as used in this disclosure refers to an arylalkyl group with an alkyl carbon atom bound with a double bond to an oxygen atom and the alkyl carbon atom is adjacent to a ring carbon atom. Examples of aroyl are benzoyl and naphthoyl, and "substituted aroyl" may refer to benzoyl or naphthoyl substituted by at least one substituent including those selected from halogen, amino, vitro, hydroxy, alkyl, alkoxy and haloalkyl on the benzene or naphthalene ring.

The term "alkylsulfonyl" as used in this disclosure refers to an alkyl group with a sulfonyl group ($-SO_2-$). Exemplary alkylsulfonyl groups include methanesulfonyl, trifluoromethanesulfonyl, 2,2,2-trifluoroethyl-1-sulfonyl, and 5-(dimethylamino)naphthalene-1-sulfonyl.

The term "arylsulfonyl" as used in this disclosure refers to an aryl group with a sulfonyl group ($-SO_2-$). Exemplary arylsulfonyl groups include p-toluenesulfonyl, p-bromobenzenesulfonyl, 2-nitrobenzenesulfonyl, and 4-nitrobenzenesulfonyl.

The term "alkanoyloxy" as used in this disclosure refers to an alkoxy group or a cycloalkyloxy group bound to a carbonyl group (i.e., C=O). Exemplary alkoxy and cycloalkyloxy groups are described hereinafter.

The term "aroyloxy" as used in this disclosure refers to an aryloxy group bound to a carbonyl group (i.e., C=O). Exemplary aryloxy groups are described hereinafter.

The term "optionally substituted CH$_2$" may refer to CHalkyl, CHaryl, CHarylalkyl or in cases where there are two substituents on the carbon, each substituent is independently an alkyl group, an aryl group, or an arylalkyl group, which are set forth herein.

As used herein, the term "substituted" refers to compounds where at least one hydrogen atom is replaced with a non-hydrogen group, provided that normal valencies are maintained and that the substitution results in a stable compound. When a compound or a R group (denoted as R$^1$, R$^2$, and so forth) is noted as "optionally substituted", the substituents are selected from the exemplary group including, but not limited to, aroyl (as defined hereinafter), halogen (e.g. chlorine, bromine, fluorine or iodine), alkyl, alkoxy (i.e. straight or branched chain optionally substituted alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy (e.g., cyclopentyloxy, cyclohexyloxy, and cycloheptyloxy, aryloxy including phenoxy and phenoxy substituted with halo, alkyl, alkoxy, and haloalkyl which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl), hydrocarbyl, substituted hydrocarbyl, arylalkyl, hydroxy, oxo, alkanoyl, alkanoyloxy, amino, alkylamino, arylamino, arylalkylamino, disubstituted amines (e.g. in which the two amino substituents are selected from the exemplary group including, but not limited to, alkyl, aryl, or arylalkyl), alkanylamino, arylamino, alkanoylamino, substituted alkanoylamino, substituted arylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —SO$_2$NH$_2$), substituted sulfonamide (e.g., —SO$_2$NHalkyl, —SO$_2$NHaryl, —SO$_2$NHarylalkyl or in cases where there are two substituents on the nitrogen, each substituent is independently an alkyl, an aryl, or an arylalkyl), nitro, cyano, carboxy, carbamyl (e.g. —CONH$_2$), substituted carbamyl (e.g. —CONHalkyl, —CONHaryl, —CONHarylalkyl or in cases where there are two substituents on the nitrogen, each substituent is independently an alkyl, an aryl, or an arylalkyl), alkoxycarbonyl, aryl, substituted aryl, guanidine, heteroarylcarbonyl, substituted heteroarylcarbonyl, heterocyclyl, substituted heterocyclyl and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has one or more oxygen atoms bonded to the ring (i.e. as ring atoms). Preferably, said atom which is bonded to the ring selected from nitrogen or sulfur. An example of a heterocyclyl substituted with one or more oxygen atoms is 1,1-dioxido-1,3-thiazolidinyl.

The term "alkylthio" as used in this disclosure refers to a divalent sulfur with alkyl occupying one of the valencies and includes the groups methylthio, ethylthio, propylthio, butylthio, pentylthio, hexylthio, octylthio.

The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl.

The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

"Pharmaceutically acceptable salts" refer to mineral or organic acid salts of basic groups, such as amines, and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like. The pharmaceutically acceptable salts of the present disclosure can be synthesized from the active ingredient that contains a basic or acidic moiety by conventional chemical methods. Generally, such salts can be prepared by reacting the free acid or base forms of the active ingredient with a stoichiometric amount of the appropriate base or acid in water or in an organic solvent, or in a mixture of the two; generally, non-aqueous media like ether, ethyl acetate, ethanol, isopropanol, or acetonitrile are preferred. Salts may be formed when an acidic proton present in the parent compound either is replaced by a metal ion, e.g., an alkali metal ion, an alkaline earth ion, or an aluminum ion; or coordinates with an organic base such as ethanoamine, danolanine, diethanolamine, triethanolamine, tromethamine, N-methylglucamine, and the like. For example, when $R^2$ is a carboxylate group, the metal ion may be sodium, potassium, lithium, calcium, magnesium, or aluminum. In some embodiments, the metal ion is substituted by an ammonium ion.

In some embodiments, the pharmaceutically acceptable salt refers to the active ingredient containing a counter-ion. As used herein, the term "counter-ion" refers to an anion, preferably a pharmaceutically acceptable anion that is associated with a positively charged compound of Formula (1) or (2) (e.g., when $R^4$ is hydrogen, an optionally substituted alkyl group, an optionally substituted cycloalkyl, or an optionally substituted arylalkyl group, the nitrogen atom attached to $R^4$ has a positive charge). Non-limiting examples of pharmaceutically acceptable counter-ions include halides, such as fluoride, chloride, bromide, iodide, nitrate, sulfate, phosphate, amide, methanesulfonate, ethanesulfonate, p-toluenesulfonate, salicylate, malate, maleate, succinate, tartrate, citrate, acetate, perchlorate, trifluoromethanesulfonate (triflate), acetylacetonate, hexafluorophosphate, and hexafluoroacetylacetonate. In some embodiments, the counter-ion is a halide, preferably chloride.

As used herein, "analog" refers to a chemical compound that is structurally similar to a parent compound, but differs slightly in composition (e.g., one atom or functional group is different, added, or removed). The analog may or may not have different chemical or physical properties than the original compound and may or may not have improved biological and/or chemical activity. For example, the analog may be more hydrophilic or it may have altered reactivity as compared to the parent compound. The analog may mimic the chemical and/or biologically activity of the parent compound (i.e., it may have similar or identical activity), or, in some cases, may have increased or decreased activity. The analog may be a naturally or non-naturally occurring variant of the original compound. Other types of analogs include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analog" in that a parent compound may be the starting material to generate a "derivative", whereas the parent compound may not necessarily be used as the starting material to generate an "analog". A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis (Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) *Curr. Pharm. Design.* 5(4):265-287; Pauletti et al. (1997). *Adv. Drug. Delivery Rev.* 27:235-256; Mizen et al. (1998) *Pharm. Biotech.* 11:345-365; Gaignault et al. (1996) *Pract. Med. Chem.* 671-696; M. Asghamejad (2000). Improving Oral Drug Transport Via Prodrugs, in G. L. Amidon, P. 1. Lee and E. M. Topp, Eds., Transport Processes in Pharmaceutical Systems, Marcell Dekker, p. 185-218; Balant et al. (1990) *Eur. J. Drug Metab. Pharmacokinet.,* 15(2): 143-53; Balimane and Sinko (1999) *Adv. Drug Delivery Rev.,* 39(1-3):183-209; Browne (1997) *Clin. Neuropharmacol.* 20(1): 1-12; Bundgaard (1979) *Arch. Pharm. Chemi.* 86(1): 1-39; H. Bundgaard, ed. (1985) Design of Prodrugs, New York: Elsevier; Fleisher et al. (1996) *Adv. Drug Delivery Rev.* 19(2): 115-130; Fleisher et al. (1985) *Methods Enzymol.* 112: 360-81; Farquhar D, et al. (1983) *J. Pharm. Sci.,* 72(3): 324-325; Han, H. K. et al. (2000) *AAPS PharmSci.,* 2(1): E6; Sadzuka Y. (2000) *Curr. Drug Metab.,* 1(1):31-48; D. M. Lambert (2000) *Eur. J. Pharm. Sci.,* 11 Suppl 2:S15-27—each incorporated herein by reference in its entirety). In some embodiments, "pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. An example, without limitation, of a prodrug would be a compound of the present invention, which is, administered as an ester, phosphate, amide, carbamate, or urea.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

In a preferred embodiment, the compound represented by Formula (1) is:

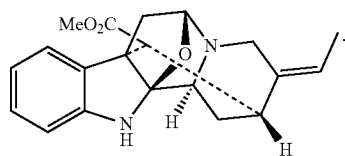 [SMILES: C/C=C1\CN2[C@H]3C[C@@H]1[C@@H](C(=O)OC)[C@]14C[C@H]2O[C@]31Nc1ccccc14]

A "pharmaceutical composition" refers to a mixture of the compounds described herein or pharmaceutically acceptable salts, or prodrugs thereof, with other chemical components, such as physiologically acceptable carriers and excipients. One purpose of a pharmaceutical composition is to facilitate administration of active ingredient to a subject. The term "composition," as used herein, refers to two or more chemical entities that are mixed together to comprise a homogenous or heterogeneous solid, liquid, or gas. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to one or more ingredients in the composition that is biologically active, for example, isopicrinine, a compound represented by Formula (1), a derivative thereof, a solvate thereof, a salt thereof, a prodrug thereof, and/or a solvate thereof, a compound represented by Formula (2), a derivative thereof, a solvate thereof, a prodrug thereof, and/or a solvate thereof.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered orally, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety.

An amount of the active ingredient may be at least 0.01 wt %, 0.05 wt %, 0.1 wt %, 0.5 wt %, 1 wt %, 2 wt %, or 3 wt %, and up to 20 wt %, 17 wt %, 14 wt %, 11 wt %, 8 wt %, or 5 wt %, based on a total weight of the pharmaceutical composition. In some embodiments, the amount of the active ingredient is more than 20 wt %, 25 wt %, 30 wt %, 35 wt %, 40 wt %, 45 wt %, 50 wt %, 55 wt %, 60 wt %, or 70 wt %, and up to 99.9 wt %, 99 wt %, or 90 wt %. The amount of active ingredient that can be combined with the carrier materials to produce a single dosage form varies depending upon the mammalian subject treated and the particular mode of administration.

The at least one exogenous pharmaceutically acceptable carrier and/or excipient may be an organic solvent, a synthetic polymer, a fatty acid, a synthetic fatty ester, a vegetable oil, and a surfactant. The following carriers and excipients are not found in *Rhazya stricta*.

Exemplary organic solvents include, without limitation, the organic solvents and organic acids described herein in addition to glycol ethers (e.g. 1,2-dimethoxyethane, diglyme, triglyme), alkyl methyl sulfoxide (e.g., dimethyl sulfoxide, decylmethyl sulfoxide, tetradecylmethyl sulfoxide), ketone (e.g., acetone, butanone), esters (e.g. ethyl acetate, propyl acetate), an amide/lactam (e.g. dimethylformamide, dimethylacetamide, pyrrolidone, N-methyl-2-pyrrolidone, N-(2-hydroxyethyl) pyrrolidone), acetonitrile, propionitrile, butyronitrile, benzonitrile, ethylene carbonate, propylene carbonate, 1,3-dimethyl-3,4,5,6-tetrahydro-2(1H)-pyrimidinone, and mixtures thereof.

Exemplary synthetic polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (maleic anhydride), a polyvinyl alcohols, and copolymers, terpolymers, or combinations or mixtures therein. The copolymer/terpolymer may be a random copolymer/terpolymer, or a block copolymer/terpolymer.

The polylactide may be a polymerization product of L-lactide, D-lactide, or mixtures thereof. The tacticity of the polylactide polymer may be syndiotactic, atactic, or preferably, isotactic. As used herein, the term "tacticity" refers to the relative orientation of each methyl group in a repeating unit of polylactide polymer relative to the methyl groups in neighboring monomer units. In isotactic polylactide all the methyls are located on the same side of the polymer backbone. In syndiotactic polylactide, the methyls have alternate positions along the chain. In atactic polylactide, the methyls are placed randomly along the chain. Tacticity may be measured directly using proton or carbon-13 NMR, x-ray powder diffraction, secondary ion mass spectrometry (SIMS), vibrational spectroscopy (FTIR) and especially two-dimensional techniques. Tacticity may also be inferred by measuring another physical property, such as melting temperature, when the relationship between tacticity and that property is well-established.

Lactic acid-based polymers, and copolymers of lactic acid and glycolic acid (PLGA), including poly(D,L-lactide-co-glycolide) and poly(L-lactide-co-glycolide) may be preferred. In some embodiments, the PLGA polymers have a weight average molecular weights of between about 2,000 to about 100,000 and monomer ratios of lactic acid to glycolic acid of between about 50:50 to about 100:0.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to an monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide. A particular polyoxyethylene sorbitan fatty ester is polyoxyethylene 20 sorbitan monooleate also known as polysorbate 80 or Tween 80 (T80).

Surfactants may act as detergents, wetting agents, emulsifiers, foaming agents, and dispersants. Surfactants that can be present in the disclosed compositions include anionic surfactants, amphoteric surfactants, cationic surfactants, zwitterionic surfactants, non-ionic surfactants, and combinations thereof. Surfactants suitable for use in the present invention may include TWEEN®, polyethylene glycol (PEG), PLURONICS™, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, nonoxynol 30, and polysorbates such as polysorbate 20, polysorbate 40, polysorbate 60 or polysorbate 80.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the active ingredient or other components of the pharmaceutical composition in which it is contained. The term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

A non-limiting example of a pharmaceutical carrier for the active ingredient disclosed herein is a co-solvent system, such as the VPD co-solvent system, containing benzyl alcohol, a non-polar surfactant, a water-miscible organic polymer, and an aqueous phase. VPD is a solution containing: 1-10% w/v, 2-8% w/v, or 3-4% w/v benzyl alcohol; 4-20% w/v, 5-15% w/v, or 8-10% w/v of the nonpolar surfactant polysorbate 80; and 50-70% v/v, 55-65% w/v, or 64-65% w/v polyethylene glycol 300; each based on a total volume of the solution and VPD is made up to volume in absolute ethanol. The VPD co-solvent system (e.g., VPD: D5W) may be prepared by diluting the VPD solution with a solution containing dextrose in an amount ranging from 1-10% w/v, 2-8% w/v, or 3-5% w/v dextrose, based on a total volume of the solution. A volume ratio between the VPD solution to the solution containing dextrose may be 5:1 to 1:5, 3:1 to 1:3, or 2:1 to 1:2. This co-solvent system dissolves compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Another aspect of the disclosure relates to a method of treating cancer in a subject in need thereof, the method comprising administering an effective amount of the active ingredient to the subject. The effective amount of the active ingredient may be in a range of 1-100 mg/kg body weight of the subject, 5-60 mg/kg, or 10-30 mg/kg. In most embodiments, the active ingredient is administered in the form of the pharmaceutical composition described herein. The cancer may be lung cancer, stomach cancer, colon cancer, liver cancer, ovarian cancer, kidney cancer, breast cancer, prostate cancer, uterus cancer, melanoma, esophageal cancer, brain cancer, pancreatic cancer, and combinations thereof. Preferably, the cancer is breast cancer and/or pancreatic cancer. In some embodiments, the neoplastic activity of the tumor or cancer cells may be localized or initiated in one or more of the following: blood, bladder, cervix, rectum, intestine, spleen, head, neck, testicle, bone (including bone marrow), thyroid gland, and central nervous system.

In treating certain cancers, the best approach is a combination of surgery, radiotherapy, and/or chemotherapy. Therefore, in at least one embodiment, the composition is employed with radiotherapy. In another embodiment, the composition is employed with surgery. The radiotherapy and/or surgery may be before or after the composition is administered.

The active ingredient can be used in combination with one or more other chemotherapeutic agents. The dosage of the active ingredient and/or the chemotherapeutic agent may be adjusted for any drug-drug reaction. The composition may contain 0.1-50 wt % of the chemotherapeutic agent, preferably 10-40 wt %, more preferably 10-20 wt %, relative to the weight of the active ingredient. In one embodiment, the chemotherapeutic agent is at least one of a mitotic inhibitor; an alkylating agent; an anti-metabolite; a cell cycle inhibitor; an enzyme; a topoisomerase inhibitor such as CAMP-TOSAR (irinotecan); a biological response modifier; an anti-hormone; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; methylhydrazine derivative, e.g., procarbazine; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Examples of alkylating agents include, without limitation, fluorouracil (5-FU) alone or in further combination with leukovorin; other pyrimidine analogs such as UFT, capecitabine, gemcitabine and cytarabine; the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents include, without limitation, folic acid analogs, e.g., methotrexate (used in the treatment of acute lymphocytic leukemia, choriocarcinomna, mycosis fungoides, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-11 inhibitors include Vioxx, CELEBREX (celecoxib), valdecoxib, paracoxib, rofecoxib, and COX 189.

Some examples of MMP inhibitors useful are AG-3340, RO 32-3555, RS 13-0830, and compounds such as 3-[[4-(4-fluorophenoxy)-benzenesulfonyl]-(1-hydroxycarbamoyl-cyclopentyl)-amino]-propionic acid; 3-exo-3-[4-(4-fluorophenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methylpiperidine-2-carboxylic acid hydroxyamide; 4-[4-(4-fluorophenoxy)-benzenesulfonylamino]-tetrahydro-pyran-4-carboxylic acid hydroxyamide; 3-[[4-(4-fluoro-phenoxy)benzenesulfonyl]-(1-hydroxycarbamoyl-cyclobutyl)-amino]-propionic acid; 4-[4-(4-chloro-phenoxy)benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluorophenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

The composition may comprise other chemotherapeutic agents, including, but not limited to, agents capable of enhancing antitumor immune responses, such as CTLA4 (cytotoxic lymphocyte antigen 4) antibodies, other agents capable of blocking CTLA4, trastuzumab, cetuximab, panitumumab, rituximab, bevacizumab, mapatumumab, conatumumab, and lexatumumab.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The active ingredient may be administered in a single dose or multiple individual divided doses. In some embodiments, the active ingredient is administered at various dosages (e.g. a first dose with an effective amount of 50 mg/kg and a second dose with an effective amount of 10 mg/kg). In some embodiments, the interval of time between the administration of the active ingredient and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the active ingredient and methods described herein. In preferred embodiments, the active ingredient and/or the composition described herein are administered orally.

The terms "patient", "subject", and "individual" are used interchangeably. As used herein, they refer to individuals suffering from a disease and encompass mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In preferred embodiments, the subject is a human.

A subject in need of treatment includes a subject already with the disease, a subject which does not yet experience or exhibit symptoms of the disease, and a subject predisposed to the disease. In preferred embodiments, the subject is a person who is predisposed to cancer, e.g. a person with a family history of cancer. Women who have (i) certain inherited genes (e.g. mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. The subject may be at a higher risk of developing pancreatic cancer when the subject is: (i) older than 45, (ii) a male, (iii) black or of Ashkenazi Jewish heritage, (iv) obese, (v) taking part in unhealthy habits such as smoking and heavy drinking, and/or (vi) diabetic. In some embodiments, the subject may be at a higher risk of developing pancreatic cancer when a family member of the subject has inherited one or more of the following conditions: hereditary pancreatitis, Peutz-Jeghers syndrome, familial malignant melanoma and pancreatic cancer, hereditary breast and ovarian cancer syndrome, and Lynch syndrome. In some embodiments, the subject may be at a higher risk of developing pancreatic cancer when the subject has one or more of the following conditions: Li-Fraumeni syndrome, familial adenomatous polyposis, chronic pancreatitis, and Hepatitis B.

In another embodiment, the subject refers to a cancer patient who has been previously administered/treated with cisplatin and have cisplatin resistance (for example in the form of high ERCC1 mRNA levels, overexpression of HER-2/neu, activation of the PI3-K/Akt pathway, loss of p53 function, and/or overexpression of antiapoptotic bcl-2).

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include but are not limited to CT scan, MR, DCE-MRI and PET scan.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the active ingredient as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly.

In most embodiments, the method further comprises measuring a concentration of a biomarker and/or detecting a mutation (e.g., methylation) in a biomarker before and/or after the active ingredient is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary cancer biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERP3. Specifically, potentially predictive cancer biomarkers include, without limitation, mutations in genes BRCA1 and BRCA2 for breast cancer. Cancer biomarkers may be useful in determining the aggressiveness of an identified cancer as well as its likelihood of responding to the treatment. Examples of such prognostic biomarkers include, without limitation, elevated expression of estrogen receptor (ER)

and/or progesterone receptor (PR), which are associated with better overall survival in patients with breast cancer.

Exemplary cancer biomarkers for pancreatic cancer include, without limitation, CA19-9, KRAS, CD1D, KCNK12, CLEC11A, NDRG4, IKZF1, PKRCB, KRAS, ppENK, cyclin D2, sparc-7, osteonectin, and TSLC1.

The mutation in the biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art.

The concentration of the biomarker may be measured with an assay, for example an antibody-based method (e.g. an ELISA). As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like.

Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used.

The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term "sample" includes any biological sample taken from the subject including cells, a tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor.

In some embodiments, the mutation in the biomarker is detected before administrating the composition to identify subjects predisposed to the disease. For example, women with a BRCA1 germline mutation are at a higher risk of contracting breast and ovarian cancer.

In some embodiments, the concentration of the biomarker is measured before and after the administration. When the concentration of the biomarker is maintained, the method may further comprise increasing the effective amount of the active ingredient by at least 5%, at least 10%, or at least 30%, up to 50%, up to 60%, or up to 80% of an initial effective amount that is in a range of 1-100 mg/kg based on the weight of the subject. The increased effective amount may be in a range of 1.05-180 mg/kg, preferably 15-140 mg/kg, more preferably 25-90 mg/kg. The subject may be administered with the increased dosage for a longer period (e.g. 1 week more, 2 weeks more, or 2 months more) than the duration with the initial effective amount.

In some embodiments, the biomarkers are measured/detected after the administering of each dose. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

In some embodiments, the ability of the active ingredient to reduce the viability of cancer cells may be determined by contacting a cytotoxic effective amount of the active ingredient with the cancer cells and then performing cell viability assays. Examples of such assays include, without limitation, ATP test, Calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. In a preferred embodiment, a MTT assay is used.

The cytotoxic effective amount of the active ingredient may be in a range of 0.01-300 µM, 0.1-270 µM, 1-240 µM, 10-200 µM, or 50-150 µM. As used herein, the term "cytotoxic effective amount" refers to a concentration of the active ingredient that reduces the viability of the cancer cells by at least 5%, 10%, 15%, 20%, 30%, 40%, 50%, 60%, 70%, 80% or 90%, relative to cancer cells not treated with the active ingredient. The reduction in viability may occur not more than 10 days, 7 days, 5 days, 3 days, or 2 days after the active ingredient is contact with the cancer cells. In one embodiment, the cytotoxic effective amount may be the $IC_{50}$ which is a concentration of the active ingredient which causes the death of 50% of cancer cells in 72 hours (3 days).

In at least one embodiment, the cancer cells are human cancer cells. The cancer cells may be derived from commercial cell lines, such as HeLa cervical cancer cells, A549 lung cancer cells, HCT15 colon cancer cells, HCT8 or HRT8 colon cancer cells, HCT116 colon cancer cells, DLD1 colon cancer cells, MCF7 breast cancer cells, MDA-MB231 breast cancer cells, A2780 ovarian cancer cells, HePG2 liver cancer cells, AsPC1 pancreatic cancer cells, PANC1 pancreatic cancer cells, and DU145 prostatic cancer cells. In some embodiments, cisplatin-resistant cancer cells are used. These cells may be cultured with low doses of cisplatin in order to build resistance to cisplatin while maintaining cell viability. Examples of cisplatin-resistant cancer cells include, but are not limited to, A2780-cis cisplatin-resistant ovarian cancer cells and SGC7901-cis cisplatin-resistant gastrointestinal cancer cells. In other embodiments, the human cancer cells are cancer cells of a human patient who has been diagnosed with at least one form of cancer, preferably breast cancer and/or pancreatic cancer.

In some embodiments, the active ingredient may be selective toward cancer cells and is non-toxic toward normal (i.e., non-cancerous) cells. In the context of the disclosure, the term "non-toxic" means that the active ingredient does not inhibit the proliferation of the normal cells relative to DMSO. Exemplary normal cells include, without limitation, primary epidermal keratinocytes, primary gingival keratinocytes, primary bladder epithelial cells, primary bronchial/tracheal epithelial cells, and primary mammary epithelial cells. The primary cells may be obtained from the American Type Culture Collection (ATCC).

The present embodiments are being described with reference to specific examples and are included to illustrate but not limit the scope of the invention.

Example 1 Extraction and Purification of Alkaloids from Rhazya Stricta

The plant leaves were collected from the Bahrah region, 30 km from Jeddah, Saudi Arabia. The identity of the plant was authenticated by a senior botanist and a sample was deposited to the herbarium repositories in the Department of Biological Sciences, King Abdulaziz University, Jeddah, Saudi Arabia.

Phytochemical components of Rhazya stricta are known to contain more than 100 alkaloids with diverse and complex structures with wide range of biological activities. The alkaloids may be akuammidine, antirhine, 3-epi-antirhine, aspidosespermidine, condylocarpine, dihydrocorynantheol, eburnamenine, eburnamine, eburnamonine, geissoschizine, isositsirikine, 16-epi-z-isositsirikine, leuconolam, rhazinilam, tetrahydrosecamine, presecamine, sewarine, stemmadenine, strictamine, strictosamide, strictosidine, tabersonine, tetrahydroalstonine, vallesiachotamine, aspidospermiose, bhimberine, bhimbhrine n-oxide, rhazimine, rhazimanine, rhazicine, leepacine, 2-methoxy-1,2-dihydrorhazimine, hr-1, vincanicine, rhazinaline, beta-sitosterol, ursolic acid, stigmasterol, oleanolic acid, rhazidigenine, n-methylleuconolam, (+)-quebrachamine, polyneuridine, (+)-vincadiformine, (−)-vincadiformmine, secamine, vincadine, bis-strictidine, 3,14-dehydrorhazigine, 16-hydrorhazisidine, rhazisidine, isorhazicine, rhazigine, strictisidine, strictamine-n-oxide, strictigine, strictine, stricticine, strictalamine, 1,2-dehydroaspidospermidine, tetrahydrosecodine, dihydrosecodine, dihydrosecamine, dihydropresecamine, tetrahydropresecamine, rhazinol, rhazimol, rhazidigenine-n-oxide, (−)16r,21r-omethyleburnamine, decarbomethoxy-15,20,16,17-tetrahydros, 1-2-dehydroasidospermidine-n-oxide, rhazizine, 15-hydroxyvincadifformine, dihydroeburnamenine, 16s,16'-decarboxytetra-hydrosecamine, nor-c-fluorocurarine, and strictibine (Obaid, A. Y., Voleti, S., Bora, R. S., Hajrah, N. H., Omer, A. M. S., Sabir, J. S. M., Saini, K. S. 2017. Cheminformatics studies to analyze the therapeutic potential of phytochemicals from Rhazya stricta. Chem. Cent. J. 11:11. DOI 10.1186/s13065-017-0240-1, incorporated herein by reference in their entirety). Some of these alkaloids have been shown to possess anti-bacterial, anticancer or wound healing activities. Recent studies have shown the potential of phytochemicals present in the leaves of Rhazya stricta plant for treatment of cancer. In order to isolate new compounds with anticancer property, total alkaloids extract (alcoholic and aqueous extract) was subjected to column chromatography using aluminium oxide column. Total of 34 individual alkaloids were thus purified and characterized. The purified alkaloids were screened for their cytotoxicity against breast and pancreatic cancer cell lines. A new alkaloid, isopicrinine, isolated from the leaves of Rhazya stricta exhibited significant cytotoxic activity toward breast and pancreatic cancer cell lines.

Preparation of Alcoholic Extract of Rhazya stricta Leaves and Purification of Indole Alkaloids:

Rhazya Stricta leaves were dried in a dark room. After that, the sample (1 kg) was crushed and extracted by chloroform:ethanol (1:2) at a room temperature for three times. The extract was concentrated under a reduced pressure to obtain a dark brown residue (102 gm of total organic extract). The total extract was then dissolved in water with 2% HCl and extracted again by chloroform to remove the non-basic compounds. The aqueous layer was neutralized by ammonium hydroxide and then extracted by chloroform. The chloroform extract was dried over anhydrous sodium sulfate followed by filtration and evaporation under a reduced pressure to obtain (20.88 gm) of crude alkaloids. Aluminium oxide column (800 gm, 80×2.5 cm) was used to purify individual alkaloids. Crude alkaloids mixture (20 gm) was homogenized with aluminium oxide (80 gm) and poured on to the top of the column and was equilibrated with chloroform. The eluents were used successively: chloroform, chloroform:ethyl acetate, and then chloroform:methanol). Fifty-milliliter fractions were collected and TLC was performed using silica-gel chromatoplates, and dragendorff as spraying agent. If the material was not homogenous, preparative thin layer silica gel chromatography (PTLC) was applied using the appropriate solvent system.

Preparation of Aqueous Extract of Rhazya stricta and Purification of Indole Alkaloids:

The plant leaves were soaked in water with 2% HCl for 3 days followed by filtration and extraction by chloroform. The aqueous layer was neutralized by $NH_4OH$ and then extracted by chloroform. The organic layer was evaporated under reduced pressure, to obtain 15 gm of water soluble alkaloids. Aluminium oxide column (750 gm, 75×2.5 cm) was used to purify indole alkaloids. The water soluble alkaloids mixture (15 gm) was homogenized with aluminum oxide (50 gm) and poured on to the top of the column containing chloroform. The eluents were used successively, i.e., chloroform, chloroform:ethyl acetate, and then chloroform:methanol. Fifty-milliliter fractions were collected and TLC was performed using silica-gel chromatoplates, and dragendorff as spraying agent. If the material was not homogenous, preparative thin layer silica gel chromatography (PTLC) was applied using the appropriate solvent system.

Example 2 Characterization of Isopicrinine (A)

The fraction eluted with a mixture of chloroform and ethyl acetate (8.5:1.5, v/v) was collected and purified by PTLC of aluminum oxide using a mixture of chloroform and methanol (9.5:0.5, v/v). The band with $R_f$=0.47 (it gave a positive response up on spraying with Dragendorff's reagent) afforded a brown oily substance (6 mg). UV $\lambda_{max}$ (MeOH) 234 nm and 286 nm; IR $\nu_{max}$ 3015 (=CH, st), 2925 (CH, st), 1734 (C=O, st) and 1610 (C=C, st) $cm^{-1}$; ESI-MS (350 ev), m/z (rel.int.): 339.1 (100) [M+H, $C_{20}H_{23}N_2O_3$], 321.0 (100) [$M^+$—OH], 309.0 (45), 289.0 (75), 279.1 (100), 216.1(25), 202.1(25), 184.1 (10), 144.0 (20), 102.1 (20) and 106.2 (45); $^1$H-NMR (Bruker WM 400 MHz) and $^{13}$C-NMR (100 MHz) in $CDCl_3$:$CD_3OD$ (1:1) (as shown in Table 1).

TABLE 1

$^1$H-NMR (400 MHz) and $^{13}$C-NMR (100 MHz) spectral data of isopicrinine

| No. | $^{13}$C-NMR $\delta_C$ | Mult. | $^1$H-NMR $\delta_H$ | Multiplicity | HMBC |
|---|---|---|---|---|---|
| 2 | 108.2 | s | — | — | 5, 3, 6α, 14β, 21β |
| 3 | 53.0 | d | 3.47 | d (4.0) | 5, 6α |
| 5 | 88.1 | d | 4.76 | d (2.8) | 21β, 6α, 6β |
| 6α | 41.1 | t | 3.45 | d (14.0) | OCH$_3$, 16, 5 |
| 6β |  |  | 2.12 | m |  |
| 7 | 54.3 | s | — | — | 6α, 6β, 15, 21α, OCH$_3$ |

TABLE 1-continued $^1$H-NMR (400 MHz) and $^{13}$C-NMR (100 MHz) spectral data of isopicrinine

| No. | $^{13}$C-NMR $\delta_C$ | Mult. | $^1$H-NMR $\delta_H$ | Multiplicity | HMBC |
|---|---|---|---|---|---|
| 8 | 134.2 | s | — | — | 12, 6α, 6β |
| 9 | 125.4 | d | 7.23 | dd (8.8, 1.2) | 11 |
| 10 | 120.9 | d | 6.70 | ddd (8.8, 8.8, 1.2) | 12 |
| 11 | 129.0 | d | 7.07 | ddd (8.8, 8.8, 1.2) | 9 |
| 12 | 111.8 | d | 6.74 | dd (8.8, 1.2) | 10 |
| 13 | 149.8 | s | — | — | 9, 11 |
| 14α | 22.4 | t | 2.04 | m | |
| 14β | | | 1.98 | m | |
| 15 | 33.0 | d | 3.57 | br s | 19, 21α, 21β, 3 |
| 16 | 53.2 | d | 2.34 | d (3.6) | 15, 3, 21β |
| 17 | 174.0 | s | — | — | 16.OCH$_3$ |
| 18 | 13.2 | q | 1.47 | dd (7.2, 2.4) | |
| 19 | 122.0 | d | 5.46 | q (7.2) | 18, 21β |
| 20 | 136.7 | s | — | — | 3, 16, 18, 21β |
| 21α | 47.0 | t | 3.75 | br.d (18.0) | |
| 21β | | | 3.21 | dt (18.0, 4.8) | |
| CO$_2$Me | 52.1 | s | 3.64 | s | 3, 15 |

The ESIMS spectrum of isopicrinine showed a base peak at m/z 338.1, which corresponded to the molecular formula, $C_{20}H_{22}N_2O_3$. The UV absorption spectra of isopicrinine showed the indoline ring UV maxima (MeOH) at 234 nm and 286 nm. The IR spectrum displayed bands at 3329 (NH, st), 3015 (=CH, st), 2925 (CH, st), 1734 (C=O, st) and 1610 (C=C, st) cm$^{-1}$. The $^1$H NMR spectrum exhibited signals for: (1) four aromatic protons characteristic for O-disubstituted benzene ring resonating at $\delta_H$ 7.23 (dd, J=8.8, 1.2 Hz, H-9), 6.70 (ddd, J=8.8, 8.8, 1.2 Hz, H-10), 7.07 (ddd, J=8.8, 8.8, 1.2 Hz, H-11), 6.74 (dd, J=8.8, 1.2 Hz, H-12); (2) an olefinic methyl group appeared at $\delta_H$ 1.47 (dd, J=7.2, 2.4 Hz, Me-18); (3) an olefinic proton signal resonating at $\delta_H$ 5.46 (q, J=7.2 Hz, H-19); and (4) a singlet at $\delta_H$ 3.64 characteristic of a methyl ester group. Table 1 summarizes the NMR spectra data.

The $^{13}$C NMR spectra of isopicrinine showed resonances of 20 carbons, which were differentiated by the DEPT NMR experiment into two methyl ($\delta_C$ 52.1 and 13.2), three methylene ($\delta_C$ 47.0, 41.1, and 22.4), nine methine ($\delta_C$ 129.0, 125.4, 122.9, 122.0, 111.8, 88.1, 53.2, 53.0 and 32.2), and six quaternary ($\delta_C$ 174.0, 149.8, 134.2, 108.2, 54.3 and 52.1) carbons.

Resonances attributable to nine carbons in the $^{13}$C NMR spectrum accounted for four carbon-carbon double bonds and one carbonyl group, implying that isopicrinine has a hexacyclic skeleton. The association of all CH$_3$, CH$_2$, and CH carbons and protons were achieved from the HSQC spectrum.

The $^1$H-$^1$H COSY spectrum supported the existence of 1,2-disubstituted benzene ring through the $^1$H-$^1$H spin system from H-9 to H-12, an ethylidine group through the correlation between the methine proton resonating at $\delta_H$ 5.46 and the methyl protons at $\delta_H$ 1.47. Furthermore, the $^1$H-$^1$H COSY spectrum established three aliphatic proton sequence H-5-H$_2$-6, H-16-H-15-H$_2$-14-H-3 and an isolated methylene protons H$_2$-21. From COSY and HMBC spectrum, the correlations of the proton H-3 ($\delta_H$ 3.47) with C-2 ($\delta_C$ 108.2) and C-14 ($\delta_C$ 22.4) suggested the linkage C-2-CH-3-CH$_2$-14-CH-15. The correlations between H-16 with C-15; C-7 and H-15 with C-20 and C-21 and H$_3$-18 with C-20 established the position of the ethyledine group and the attachments of C-15. The HMBC correlations of H-16 and Me of ester $\delta_H$ 3.64 to C-17 ($\delta_C$ 174.0) indicated the direct connection of H-16 and methyl ester to C-17, the correlation from H-5 to $\delta_C$ 108.2 supported the existence of a C$_2$—O—C$_5$ bond, which was confirmed by its 11 degree of unsaturation consistent with the molecular formula of $C_{20}H_{22}N_2O_3$, as established by ESI-MS. The downfield NMR data of CH-5 allowed the attachment of an oxygen atom and nitrogen atom (N-4) to C-5. The HMBC correlation between $\delta_H$ 3.21 H-21 and C-5 revealed the connection of N-4 with C-21, correlation between H-21 and H-18 to C-20 $\delta_C$ 136.7. In the NOSEY spectrum of compound 1, H-15 ($\delta_H$ 3.57) is correlated with H-16 ($\delta_H$ 2.34) and H-3 ($\delta_H$ 3.47) is correlated with 1H-5 ($\delta_H$ 4.76). Comparison between the above results and literature data, isopicrinine is greatly similar to picrinine (B) which was isolated from the leaves of *Alstonia scholaris* (Fumiko, A., Rong-Fuchen, Yamauchi, T., Marubayashi, N., Ueda, I. 1989. Alschomine and isoalschomine, new alkaloids from the leaves of *Alstonia scholaris*. Chem. Pharma. Bull. 37: 887-890, incorporated herein by reference in its entirety). The main differences were in the stereochemistry of C-5 and C-15: the absolute configurations of C-5 and C-15 in isopicrinine were found to be different from that of picrinine. In isopicrinine, H-3 and H-5 occupied the α-position while H-15 and H-16 occupied the 3-position.

Example 3 Cell Culture

MCF7, a breast cancer cell line was procured from the American Type Culture Collection (ATCC) and propagated in Dulbecco's Modified Eagle's medium (DMEM) supplemented with 10% (v/v) fetal bovine serum (FBS), 100 µg/ml streptomycin and 100 U/ml penicillin at 37° C. in a humidified incubator with 5% CO$_2$. Human pancreatic cell lines, AsPC1 and PANC1, were obtained from the American Type Culture Collection (ATCC). AsPC1 cell line was grown in RPMI-1640 medium supplemented with 10% (v/v) fetal bovine serum (FBS), 100 µg/ml streptomycin and 100 U/ml penicillin. PANC1 cell line was cultured in DMEM supplemented with 10% (v/v) fetal bovine serum (FBS), 100 µg/ml streptomycin and 100 U/ml penicillin.

Example 4 Cell Viability Assay

MCF7 cells (2×10$^4$ cells/well) were sub-cultured in 24-well plate and incubated at 37° C. in a humidified incubator with 5% CO$_2$ for 20 hrs. Cells were treated with 10 µg/ml and 100 µg/ml of around 34 purified alkaloid fractions (i.e. 14 alkaloid fractions from the alcoholic extract and 20 alkaloid fractions from the aqueous extract) of *Rhazya stricta* and further incubated for 18 hrs. After the drug treatment, cells were analysed under phase contrast microscope. Based on the preliminary cytotoxicity data, purified isopicrinine was selected for further analysis.

MCF7 cells (2×10$^4$ cells/well) were treated with 3 µM, 30 µM, 300 µM, 600 µM, 1.5 mM of isopicrinine at 37° C. in a humidified incubator with 5% CO$_2$ for 20 hrs. After the drug treatment, cells were analysed under phase contrast microscope. Cytotoxicity was detected at 300 µM concentration onwards in all the samples. MCF7 cells (2×10$^4$ cells/well) were treated with varying doses of isopicrinine in triplicates, i.e., 3 µM, 30 µM, 60 µM, 120 µM, 180 µM, 240 µM, 300 µM and 600 µM, at 37° C. in a humidified incubator with 5% CO$_2$ for 20 hrs and IC50 was determined. The nuclear morphological changes, which are mainly associated with apoptosis were analysed by Hoechst 33342 staining. Briefly, MCF7 cells (2×10$^4$ cells/well) were grown on coverslips and treated with 150 µM of purified alkaloid for 24 hrs. The cells were washed with Dulbecco's phosphate buffer saline (DPBS) and fixed with 100% methanol for 15 min at room temperature. Cells were washed with DPBS and stained with Hoechst 33342 for 15 min at room temperature. The cells were washed thrice with DPBS and analysed under fluorescent microscope (Nikon, Japan).

PANC1 and AsPC1 cells ($1.3 \times 10^4$ cells/well) were subcultured in 96-well plates and incubated at 37° C. in a humidified incubator with 5% $CO_2$ for 24 hrs. Varying concentrations of isopicrinine (i.e., 0, 30 μM, 75 μM, 150 μM and 300 μM were added to the cultured cells and further incubated at 37° C. in a humidified incubator with 5% $CO_2$ for 24 hrs. The cell viability was determined using MTT (3-(4,5-dimethylthiazol-2-yl)-2,5-diphenyltetrazolium bromide) assay by following the manufacturer's instructions. Briefly, 20 μl/well of MTT was added to the cells and plates were incubated for 4 hrs. After the incubation, media along with the MTT was removed and 150 μl/well of isopropanol was added and further incubated for 15 min on shaker incubator. Spectrophotometer readings were taken at 450 nm and 630 nm. This assay is based on the conversion of yellow tetrazolium salt MTT to purple formazan crystal by metabolically active cells. The amount of formazan produced is proportional to the number of viable cells.

Figures 2A, 2B, 2C:
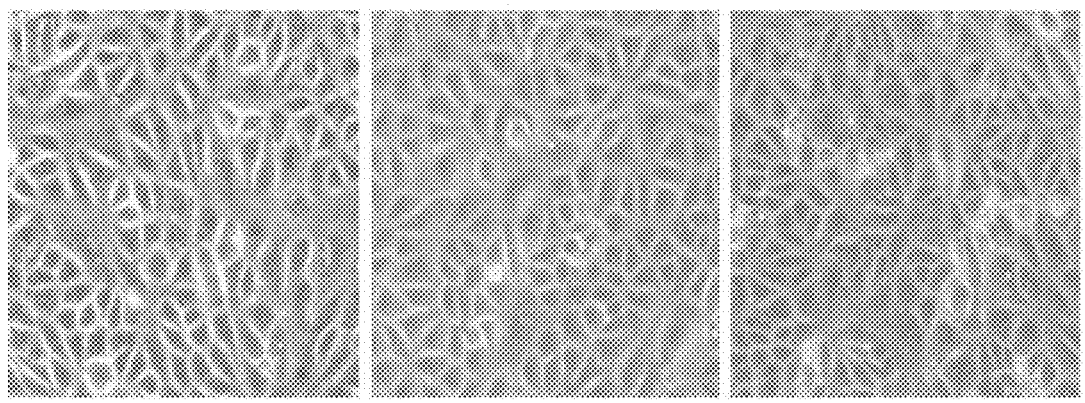
FIG. 2A is a photograph of the MCF7 breast cancer cells line treated with DMSO (control).
FIG. 2B is a photograph of the MCF7 breast cancer cells line treated with 30 μM isopicrinine.
FIG. 2C is a photograph of the MCF7 breast cancer cells line treated with 150 μM isopicrinine.
Figures 2D, 2E, 2F:
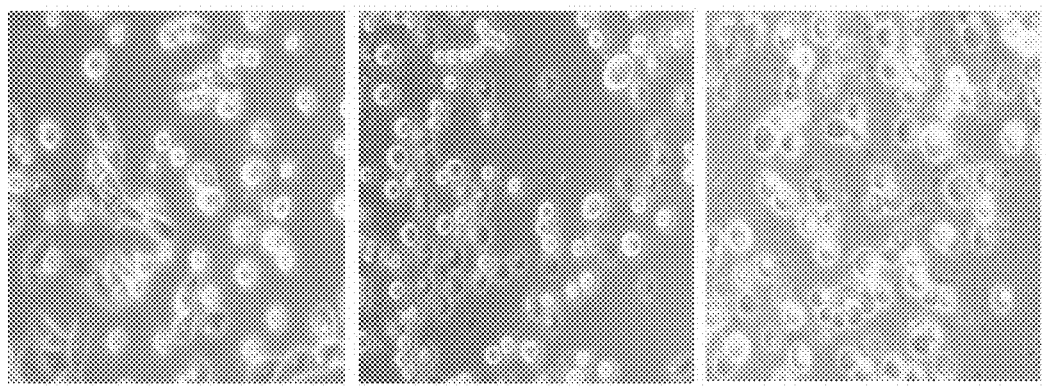
FIG. 2D is a photograph of the MCF7 breast cancer cells line treated with 300 μM isopicrinine.
FIG. 2E is a photograph of the MCF7 breast cancer cells line treated with 600 μM isopicrinine.
FIG. 2F is a photograph of the MCF7 breast cancer cells line treated with 1,500 μM isopicrinine.
Figure 3A:
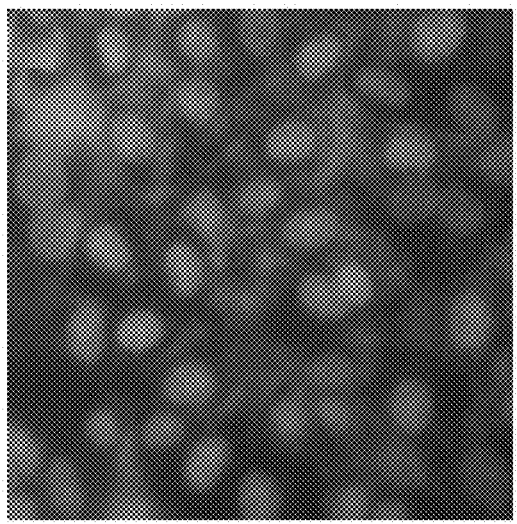
FIG. 3A is a fluorescent image of MCF7 breast cancer cells line treated with DMSO and thereafter stained with Hoechst 33342.
Figure 3B:
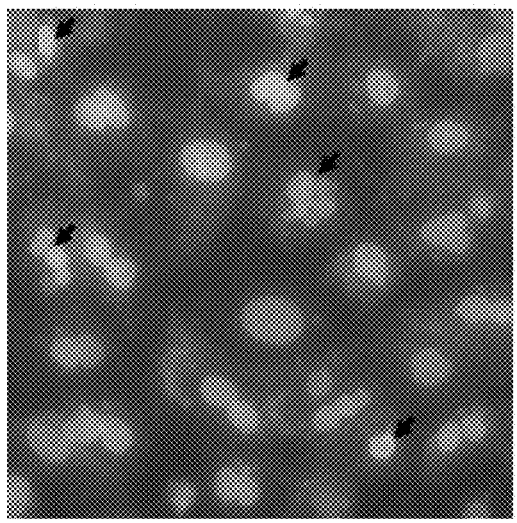
FIG. 3B is a fluorescent image of MCF7 breast cancer cells line treated with 150 μM isopicrinine and thereafter stained with Hoechst 33342.

Isopicrinine showed efficient cytotoxic activity against MCF7 cells and a IC50 value of isopicrinine was 240 μM. FIGS. 2D-2F show cell shrinkage, cellular detachment and loss of adherent morphology after treatment with high doses of isopicrinine, indicating the anticancer potential of isopicrinine. FIG. 3B shows the MCF7 cells stained with Hoechst 33342 and revealed the chromatin condensation and nuclear fragmentation in MCF7 cells, which are important features of apoptotic cell death, after treatment with isopicrinine. The arrows in FIG. 3B indicate chromatin condensation and nuclear fragmentation. Isopicrinine also showed efficient cytotoxic activity against pancreatic cancer cell lines AsPC1 and PANC1 as shown in Table 2.

TABLE 2

Cell viability data of PANC1 and AsPC1 cells treated with isopicrinine

| S.No. | Isopicrienne dose (μM) | PANC1 cell line % Cell Viability | AsPC1 cell line % Cell viability |
|---|---|---|---|
| 1 | 0 | 100 | 100 |
| 2 | 30 | 74.52 | 87.71 |
| 3 | 75 | 70.75 | 55.9 |
| 4 | 150 | 69.62 | 53.49 |
| 5 | 300 | 64.6 | 42.41 |

Example 5 RNA-Sequencing Studies

MCF7 cells ($1.6 \times 10^5$ cells) were treated with varying doses (sub-lethal) of purified isopicrinine i.e., 30 μM and 150 μM, in triplicates, for 18 hrs at 37° C. Total RNA was extracted using TRIzol reagent. Gene expression analyses of drug-treated MCF7 cells in the presence of sub-lethal concentrations of isopicrinine were performed using Illumina HiSeq. Each RNA was ribo-depleted (Ribo-Zero, Epicentre) prior to cDNA libarary preparation (ScriptSeq epicenter). Each cDNA was separately barcode tagged during library preparation, and sequenced in multiplex generating approximately >40 million 100 bp reads per sample for the mammalian cell line. The Illumina reads were mapped to their respective assembled reference transcriptome sequence using the mapping software TopHat and Cufflinks (Trapnell, C., Pachter, L., Salzberg, S. L. 2009. TopHat: discovering splice junctions with RNA-Seq. Bioinformatics, May 1; 25(9):1105-11. doi: 10.1093/bioinformatics/btp120, incorporated herein by reference in its entirety). Illumina read abundances mapping to each reference contig was normalized using the RPKM (reads per Kb per million reads) calculation. Differentially expressed transcripts were identified and functionally annotated using a variety of statistical analyses available via bioconductor in R language (Durinck, S., Moreau, Y., Kasprzyk, A., Davis, S., De Moor, B., Brazma, A., Huber, W. 2005. BioMart and Bioconductor: a powerful link between biological databases and microarray data analysis. Bioinformatics, 21(16), 3439-3440. doi: 10.1093/bioinformatics/bti525, incorporated herein by reference in its entirety). Clusters of differentially expressed and cycling transcripts were annotated to identify overrepresented GO/KEGG pathways (Kanehisa, M., Goto, S., Sato, Y., Furumichi, M., Tanabe, M., 2012. KEGG for integration and interpretation of large-scale molecular data sets. Nucleic Acids Res., 40 (Database issue), D109-14. doi: 10.1093/nar/gkr988, incorporated herein by reference in its entirety).

MCF7 cell line was treated with sub-lethal doses of 30 μM and 150 μM of isopicrinine. No cytotoxicity was detected at these tested doses: at low doses, isopicrinine did not result in cell death, however at such low doses, isopicrinine prevented further cell proliferation as compared to control cells treated with only DMSO. RNA-Seq transcription profiling was performed for analyzing the transcriptome profile in alkaloid treated MCF7 cells in order to evaluate the pharmacological effects of the new alkaloid isolated from *Rhazya stricta*. To identify the differentially regulated/expressed genes after treatment with isopicrinine, RNA was extracted from alkaloid treated MCF7 cells (30 μM and 150 μM doses) and DMSO-treated control cells and RNA-Seq experiment was carried out. The sequencing data were compared and analyzed to identify the differentially expressed genes in mammalian cells after treatment with isopicrinine. Compared with the DMSO-treated control cells, 148 genes were upregulated (fold change >−1; P value <0.05) and 64 genes were downregulated (fold change <−1; P value <0.05) in MCF7 cells treated with 30 μM of isopicrinine. Moreover, treatment of MCF7 cells with 150 μM of isopicrinine resulted in the upregulation of 36 genes (fold change >1; P value <0.05) and downregulation of 59 genes (fold change <−1; P value <0.05), as compared to the DMSO-treated control cells (Table 3 and 4; FIG. 4).

TABLE 3

Upregulated genes in MCF7 breast cancer cells after exposure to isopicrinine

| Functional Role | Gene | log2 (fold change) | P value | Significant |
|---|---|---|---|---|
| Induction of apoptosis | INHBA | 1.02564 | 0.0002 | yes |
| | MAGED1 | 0.895445 | 5.00E−05 | yes |
| | BBC3 | 1.48064 | 5.00E−05 | yes |
| | CDKN1A | 1.11896 | 5.00E−05 | yes |
| Response to DNA damage stimulus | GADD45A | 1.33298 | 5.00E−05 | yes |
| | BTG2 | 1.48468 | 5.00E−05 | yes |
| | DDB2 | 1.19055 | 5.00E−05 | yes |
| | CCND1 | 1.49047 | 0.00015 | yes |
| Regulation of transcription | MXI1 | 1.11765 | 0.00015 | yes |
| | EGR1 | 1.39018 | 5.00E−05 | yes |
| | ATF3 | 1.3961 | 0.00025 | yes |
| | FHL2 | 1.02376 | 5.00E−05 | yes |
| | MDM2 | 1.72451 | 5.00E−05 | yes |
| | NRG1 | 0.882487 | 0.00015 | yes |
| Regulation of | SPP1 | 1.07532 | 5.00E−05 | yes |

TABLE 3-continued

Upregulated genes in MCF7 breast cancer cells after exposure to isopicrinine

| Functional Role | Gene | log2 (fold change) | P value | Significant |
|---|---|---|---|---|
| cell growth | LTBP4 | 1.50385 | 0.0001 | yes |
| | VGF | 0.947189 | 5.00E−05 | yes |
| Cytoskeleton | AGBL2 | 2.62717 | 0.0003 | yes |
| | KRT81 | 1.79689 | 0.0004 | yes |
| | DLG2 | 2.26801 | 5.00E−05 | yes |
| | PTP4A1 | 1.33147 | 5.00E−05 | yes |
| | DRP2 | 2.04721 | 5.00E−05 | yes |

TABLE 4

Down regulated genes in MCF7 breast cancer cells after exposure to isopicrinine

| Functional role | Gene | log2 (fold change) | P value | Significant |
|---|---|---|---|---|
| Cell divsion | CDC6 | −2.32211 | 5.00E−05 | yes |
| | CDK1 | −1.14933 | 5.00E−05 | yes |
| | CDCA5 | −1.55071 | 0.0003 | yes |
| | ASPM | −1.3045 | 5.00E−05 | yes |
| | NUSAP1 | −1.53939 | 5.00E−05 | yes |
| | KIF23 | −0.904965 | 0.00035 | yes |
| | PRC1 | −1.52742 | 0.00045 | yes |
| | BIRC5 | −0.957158 | 0.0002 | yes |
| | AURKB | −1.64598 | 5.00E−05 | yes |
| | NDC80 | −1.34275 | 0.0001 | yes |
| | SGOL1 | −1.04359 | 0.0005 | yes |
| | FBXO5 | −1.06667 | 5.00E−05 | yes |
| | PTTG1 | −1.05005 | 5.00E−05 | yes |
| | NCAPH | −1.01758 | 0.00015 | yes |
| | NCAPG | −1.31394 | 5.00E−05 | yes |
| DNA replication | MCM3 | −1.64431 | 5.00E−05 | yes |
| | MCM4 | −1.52185 | 5.00E−05 | yes |
| | MCM5 | −1.87773 | 5.00E−05 | yes |
| | MCM6 | −1.42256 | 5.00E−05 | yes |
| | MCM7 | −1.71581 | 5.00E−05 | yes |
| | MCM8 | −1.01268 | 0.0001 | yes |
| | MCM10 | −1.32104 | 0.0003 | yes |
| | TOP2A | −1.66227 | 5.00E−05 | yes |
| | CDC45 | −1.80081 | 5.00E−05 | yes |
| | RFC3 | −1.14176 | 0.00045 | yes |
| | RRM2 | −1.2797 | 5.00E−05 | yes |
| Chromosone Organization | HIST2H4A | −2.13768 | 5.00E−05 | yes |
| | HIST2H2AA4, HIST2H2AC | −1.50511 | 5.00E−05 | yes |
| | HIST2H3PS2 | −1.3321 | 5.00E−05 | yes |
| | HIST2H2BF | −1.75681 | 5.00E−05 | yes |
| | HIST2H3C | −2.71641 | 0.0001 | yes |
| | HIST2H2AB | −2.14409 | 5.00E−05 | yes |
| | HIST1H2BL | −2.03159 | 0.00025 | yes |
| | HIST1H1B | −2.27766 | 5.00E−05 | yes |
| | HIST1H2AM, HIST1H3J | −2.03436 | 5.00E−05 | yes |
| | HIST1H2AJ, HIST1H2AK | −2.03436 | 5.00E−05 | yes |
| | DLGAP5 | −1.26336 | 5.00E−05 | yes |
| | ESPL1 | −1.9647 | 0.0003 | yes |
| | H2AFZ | −0.95203 | 5.00E−05 | yes |
| DNA repair | EXO1 | −1.78374 | 5.00E−05 | yes |
| | BRCA1 | −1.07641 | 0.0002 | yes |
| | UHRF1 | −1.1337 | 0.0001 | yes |
| | RAD51AP1 | −1.65155 | 5.00E−05 | yes |
| Regulation of Transcription | ATAD2 | −1.38776 | 5.00E−05 | yes |
| | MYBL2 | −1.23112 | 5.00E−05 | yes |
| | BRIP1 | −1.41617 | 5.00E−05 | yes |
| | ATAD5 | −1.62821 | 5.00E−05 | yes |

Figure 4A:
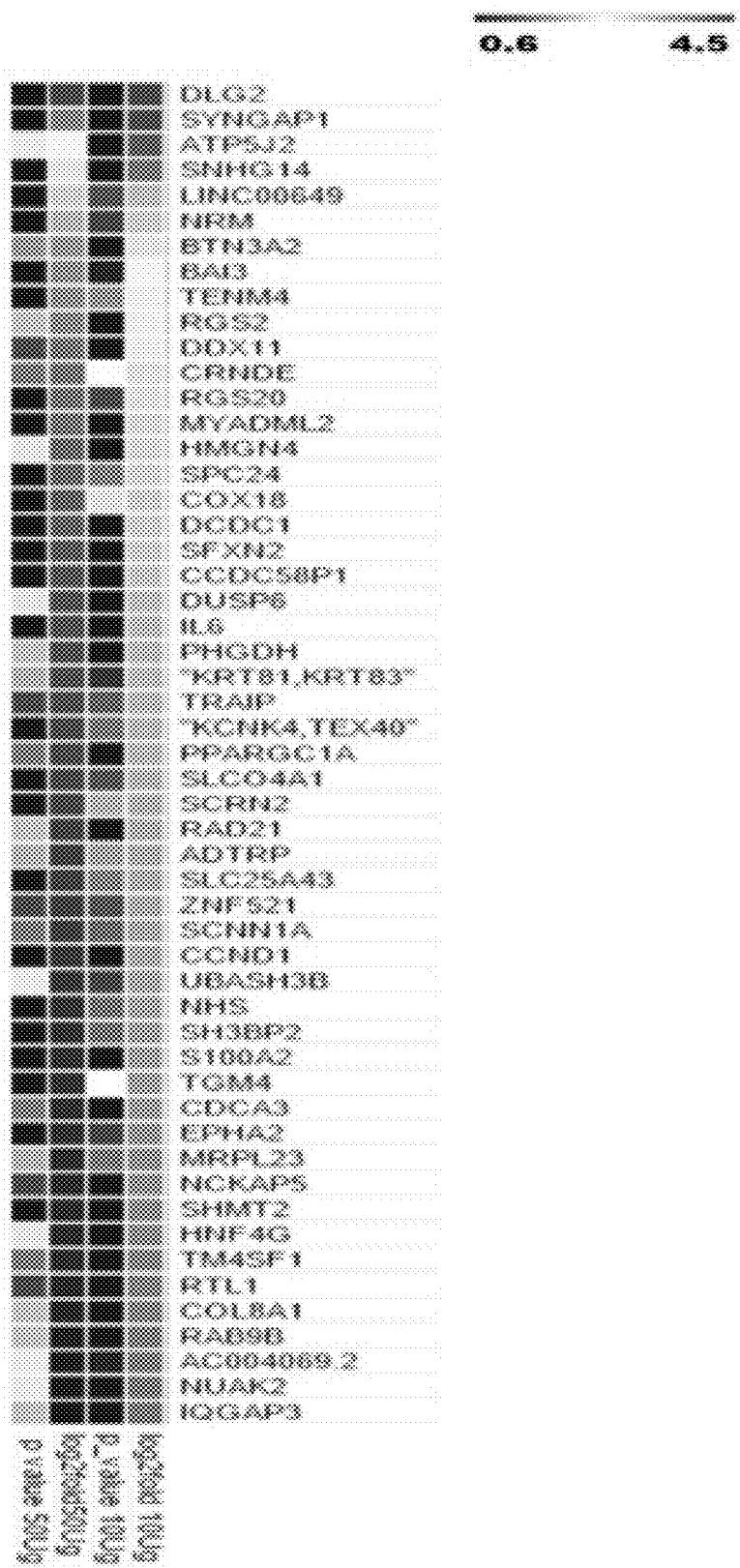
FIG. 4A shows the cluster analysis of upregulated genes from MCF7 breast cancer cells after treatment with 30 µM and 150 µM of isopicrinine compared to DMSO-treated control cells.
Figure 4B:
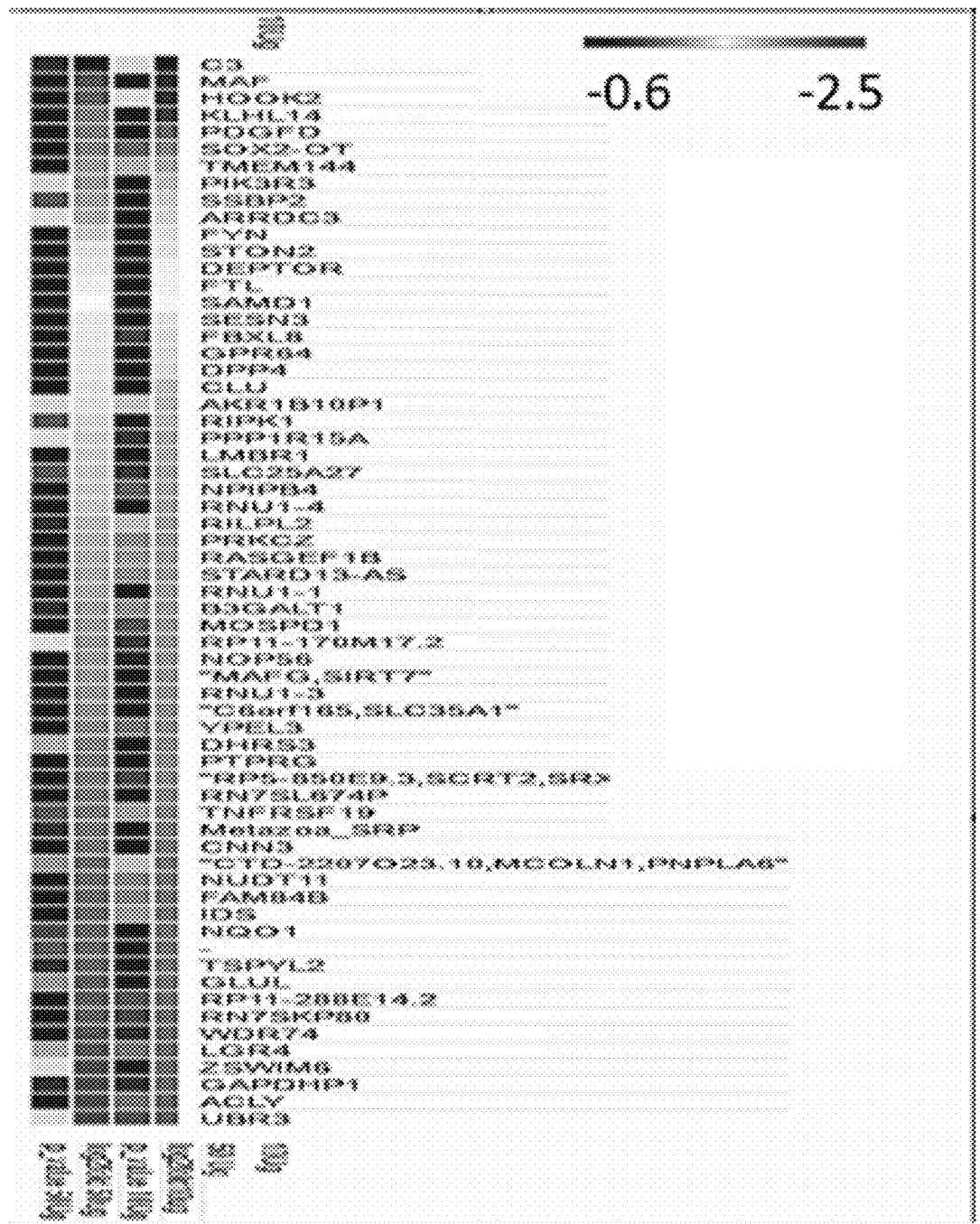
FIG. 4B shows the cluster analysis of downregulated genes from MCF7 breast cancer cells after treatment with 30 µM and 150 µM of isopicrinine compared to DMSO-treated control cells.
Figure 4C:
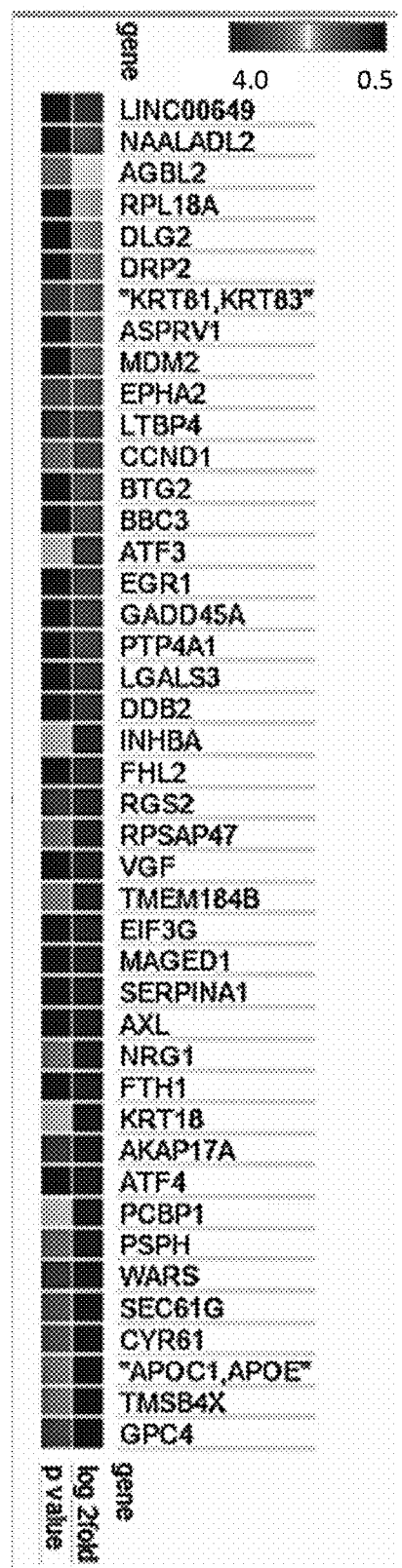
FIG. 4C shows the cluster analysis of upregulated genes from MCF7 breast cancer cells after treatment with 150 µM of isopicrinine compared to DMSO-treated control cells.
Figure 4D:
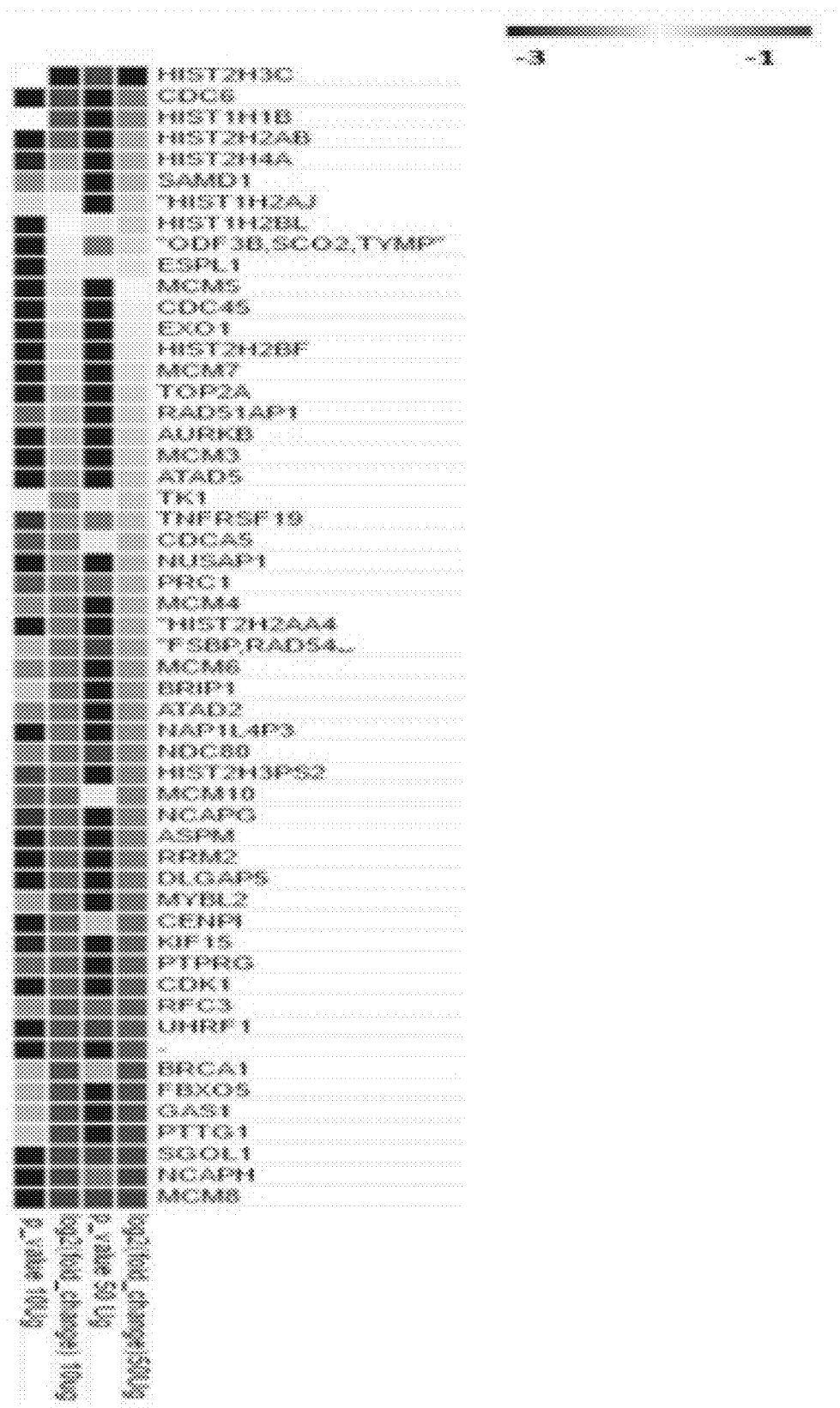
FIG. 4D shows the cluster analysis of downregulated genes from MCF7 breast cancer cells after treatment with 150 µM of isopicrinine compared to DMSO-treated control cells.

Various genes involved in DNA replication, mitosis (cell cycle), cell proliferation were found to be downregulated in MCF7 cells after treatment with isopicrinine (see Table 4 and FIGS. 4B and 4D). Genes involved in regulation of growth and cell signaling and key pro-apoptotic genes were found to be upregulated (see FIGS. 4A and 4C).

Figure 5:
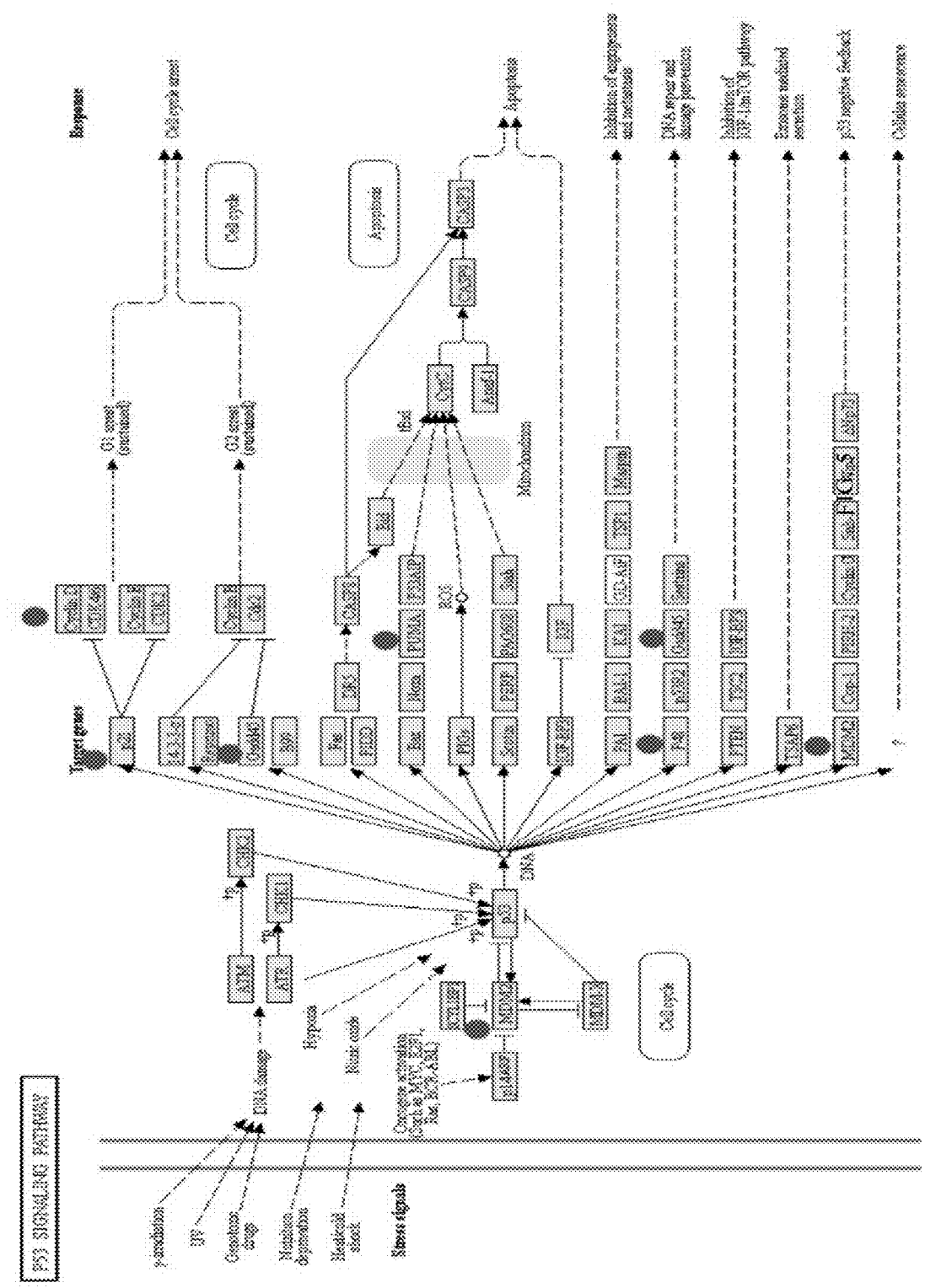
FIG. 5 shows the KEGG pathway analysis of differentially regulated genes in MCF7 cells after treatment with isopicrinine, depicting the affected genes in p53 signaling pathway.

One of the important pro-apoptotic gene, PUMA (p53 upregulated modulator of apoptosis), also known as BBC3 (Bcl-2-binding component 3), was upregulated in MCF7 breast cancer cell line after treatment with the alkaloid (see FIG. 5). The PUMA gene is a member of the Bcl-2 protein family and is involved in p53-dependent and -independent apoptosis (Nakano, K., Vousden, K. H. 2001. PUMA, a novel proapoptotic gene, is induced by p53. Mol. Cell, 7: 683-694; and Zhang, L. N., Li, J. Y., Xu, W. 2013. A review of the role of Puma, Noxa and Bim in the tumorigenesis, therapy and drug resistance of chronic lymphocytes leukemia. Cancer Gene Thera. 20: 1-7, each incorporated herein by reference in their entirety). The expression of PUMA is controlled by tumor suppressor p53 and upon activation, PUMA interacts with anti-apoptotic Bcl-2 family members and hence releases Bax or Bak, which leads to mitochondrial outer membrane permeabilization.

Following mitochondrial dysfunction, caspases are activated which finally leads to apoptotic cell death (Jabbour, A. M., Heraud, J. E., Daunt, C. P., Kaufmann, T., Sandow, J., O'Reilly, L. A., et al., 2009. Puma indirectly activates Bax to cause apoptosis in the absence of Bid and Bim. Cell Death Differ. 16: 555-563; and Yee, K. S., Wilkinson, S., James, J., Ryan, K. M., Vousden, K. H. 2009. PUMA- and Bax-induced autophagy contributes to apoptosis. Cell Death Differ. 16: 1135-1145, each incorporated herein by reference in their entirety). Induction of PUMA gene after exposure to sub-lethal dose of the alkaloid clearly suggested the potential of isopicrinine as a potential drug target for controlling tumor development.

The Mxi1 gene, encodes for the Max-interacting protein 1, was found to be significantly upregulated in MCF7 cells after treatment with the alkaloid. Mxi1 protein acts as a tumor suppressor and negatively regulates c-Myc activity. Expression of the oncogenic c-Myc gene is very strongly controlled in normal cells, however it is found to be deregulated in various types of human cancer. Myc protein interacts and dimerizes with Max transcription factor and regulates the expression of various genes involved in cell division and apoptosis. Mxi1 protein inhibits the activity of Myc by competing for Max protein and hence prevents the tumor growth. Defects in Mxi1 gene are frequently detected in prostate cancer patients (Erichsen, D. A., Armstrong, M. B., Wechsler, D. S. 2015. Mxi1 and Mxi1-0 antagonize N-Myc function and independently mediate apoptosis in neuroblastoma. Trans. Oncol. 8(1):65-74, incorporated herein by reference in its entirety).

Downregulation of survivin, which is a member of IAP (inhibitor of apoptosis) family, was detected in MCF7 cells after treatment with sub-lethal doses of isopicrinine. Survivin is known to play a key role in negative regulation of apoptosis and is also known as baculoviral inhibitor of apoptosis repeat-containing 5 (BIRC5). Exposure of high doses of isopicrinine in MCF7 cells led to the downregulation of BIRC5 gene which encodes for survivin. Survivin inhibits the caspase activation (Varughese, R. K., Torp, S. H. 2016. Survivin and gliomas: A literature review. Oncol. Lett. 12: 1679-1686, incorporated herein by reference in its entirety). Tamm and colleagues have demonstrated that survivin inhibited both Bax and Fas-induced apoptotic pathways (Tamm, I., Wang, Y., Sausville, E., Scudiero, D. A., Vigna, N., Oltersdorf, T., Reed, J. C. 1998. IAP-family protein survivin inhibits caspase activity and apoptosis induced by Fas (CD95), Bax, caspases, and anticancer drugs. Cancer Res. 58 (23): 5315-20, incorporated herein by reference in its entirety). It has been observed that silencing of survivin expression leads to increase in apoptotic cell death and subsequent decrease in tumor growth. Moreover, expression of survivin protein is found to be highly upregulated in almost all types of human cancer and also in fetal tissue, but is not expressed in normal adult cell, hence making it an attractive drug target for cancer therapy. Tamm and colleague reported the expression of survivin in all the 60 different human cancer cell lines that are being used in the National Cancer Institute's cancer drug-screening program, with the maximum level of expression in breast and lung cancer cell lines. The mechanism of survivin regulation is still not well characterized, but its regulation seems to be linked to p53 protein and is also a target gene of the Wnt pathway. The gene expression profiling data disclosed herein suggested that new alkaloid from Rhazya stricta might be inducing apoptosis in MCF7 breast cancer cell line by downregulating the expression of survivin.

Figure 6A:
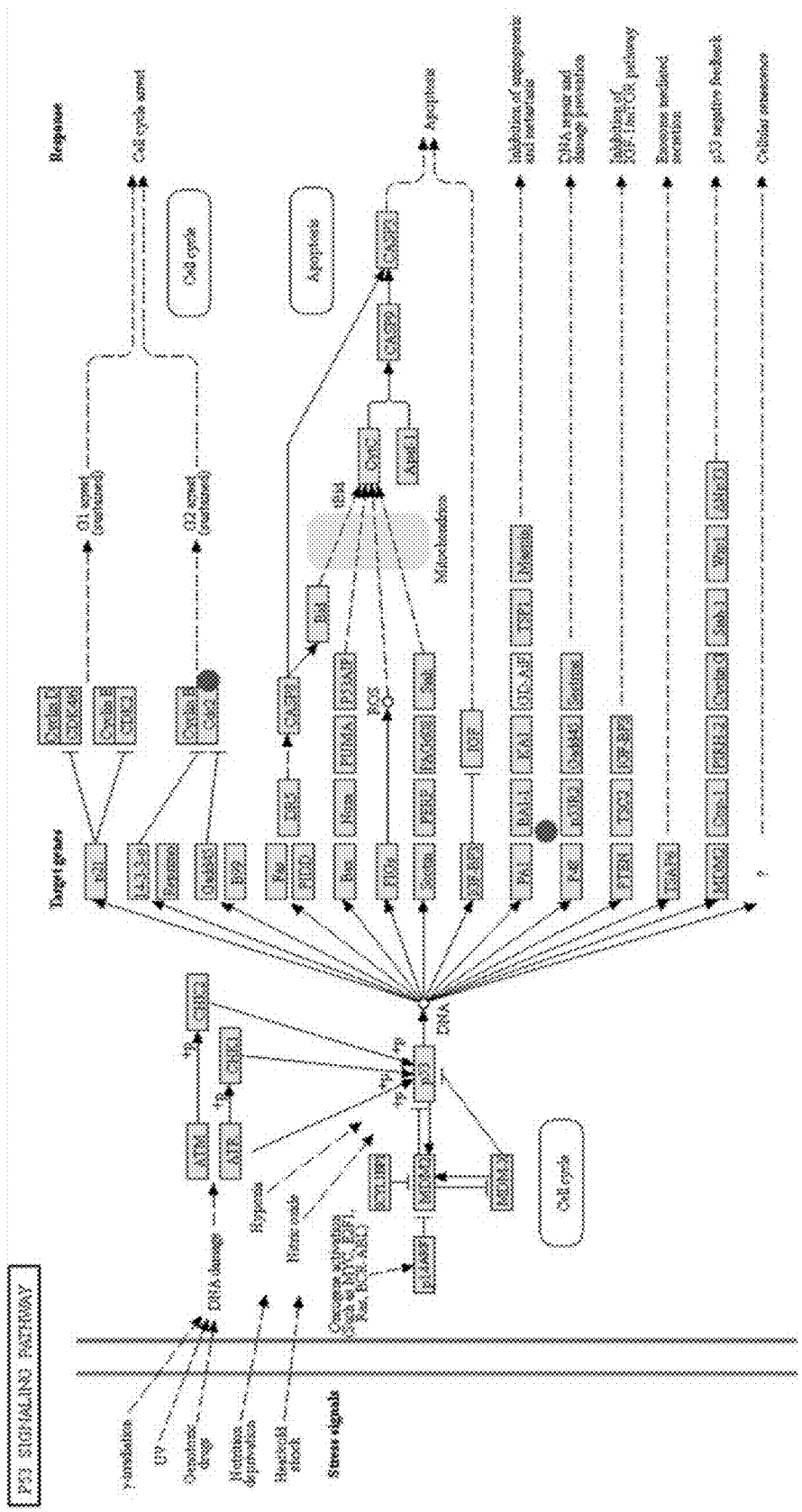
FIG. 6A shows the KEGG pathway analysis of differentially regulated genes in MCF7 cells after treatment with isopicrinine.
Figure 6B:
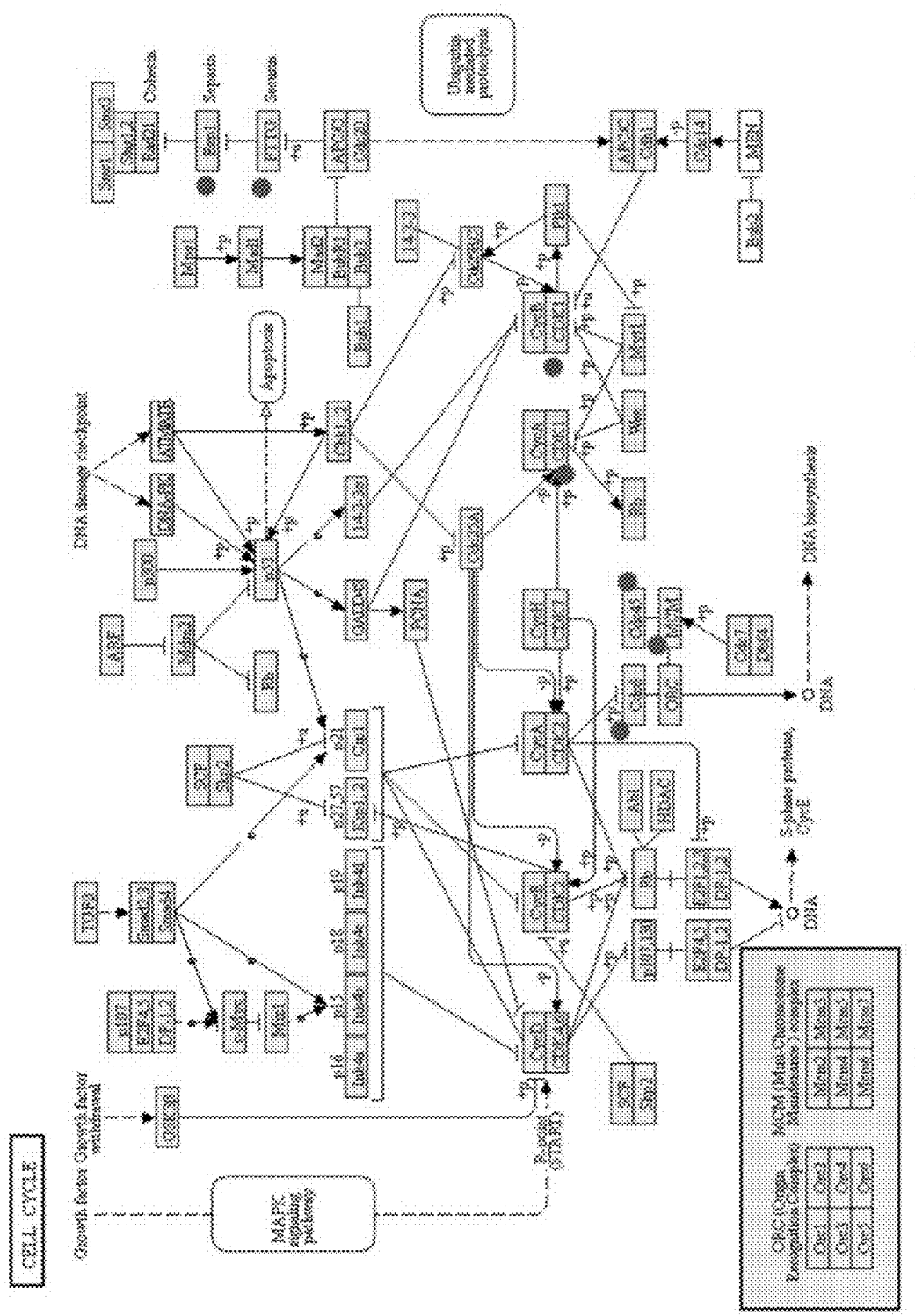
FIG. 6B shows the KEGG pathway analysis of differentially regulated genes in MCF7 cells after treatment with isopicrinine.

Genes involved in cell cycle and cell proliferation, such as CDC6, CDK1, CDCA5, DLGAP5, NUSAP1, KIF23, PRC1, BIRC5, AURKB, NDC80, CDC45, were significantly downregulated after the exposure with the sub-lethal dose of 150 µM of isopicrinine (see Table 4; FIGS. 5, 6A, and 6B). However, these genes were not affected at a low concentration (30 µM) of isopicrinine.

Further, genes which play crucial role in cell division and mitosis, such as PTTG1, DLGAP5, Cdc6, NDC80, KIF15, KIF23, PRC1, NUSAP1, Aurora B kinase, CDCA5 and ATAD2 were also found to be downregulated after the treatment of MCF7 cells with the high dose of the alkaloid. Cdc 6 (cell division cycle 6) plays an important role in regulation of DNA replication and is required for stacking mini chromosome maintenance (MCM) proteins onto the DNA during the initiation of DNA synthesis (Petrakis, T. G., Vougas, K., Gorgoulis, V. G. 2012. Cdc6: a multi-functional molecular switch with critical role in carcinogenesis. Transcription 3: 124-129, incorporated herein by reference in its entirety). Cdc6 protein has been shown to possess proto-oncogenic activity as its overexpression leads to inhibition of INK4/ARF tumor suppressor genes. Moreover, Cdc6 is found to be highly upregulated in various cancer such as lung cancer, brain cancer and cervical cancer (Murphy, N., Ring, M., Heffron, C. C., Martin, C. M., McGuinness, E., Sheils, O., O'Leary, J. J. 2005. Quantitation of CDC6 and MCM5 mRNA in cervical intraepithelial neoplasia and invasive squamous cell carcinoma of the cervix. Mod. Pathol. 18(6):844-849, incorporated herein by reference in its entirety). KIF-15 gene encodes for kinesin family member 15 protein, a motor protein that is involved in maintaining half spindle separation. KIF15 interacts with microtubules and actin filaments in dividing cells. This motor protein is found to be over-expressed in various tumors including breast cancer (Rath, O., Kozielski. 2012. Kinesins and cancer. Nature Review, 12:527-539, incorporated herein by reference in its entirety). Similarly KIF23 is involved in chromosomes movement during cell division. It has been demonstrated that KIF23 is involved in the formation and proliferation of gliomas in mice (Takahashi, S., Fusaki, N., Ohta, S., Iwahori, Y., Iizuka, Y., Inagawa, K., Kawakami, Y., Yoshida, K., Toda, M. 2012. Downregulation of KIF23 suppresses glioma proliferation. J. Neurooncol. 106 (3): 519-29, incorporated herein by reference in its entirety). DLGAP5 gene encodes for disks large-associated protein 5, also known as hepatoma upregulated protein (HURP). This protein is involved in stabilizing microtubules in proximity of chromosomes and controlling spindle dynamics during cell division. Studies have shown that over-expression of DLGAP5 led to hepatocellular carcinoma by promoting cell proliferation. RNAi mediated silencing of DLGAP5 effectively inhibited the proliferation and metastasis of hepatocellular carcinoma cells (Liao, W., Liu, W., Yuan, Q., Liu, X., Ou, Y., He, S., Yuan, S., Qin, L., Chen, Q., Nong, K., Mei, M., Huang, J. 2013. Silencing of DLGAP5 by siRNA significantly inhibits the proliferation and invasion of hepatocellular carcinoma cells. PLOS One, 8 (12): e80789, incorporated herein by reference in its entirety). Another important gene found to be downregulated by high dose of isopicrinine is ATAD2 (ATPase Family, AAA Domain Containing 2). The protein encoded by this gene is involved in the estrogen-induced cell proliferation of breast cancer cells (Zou, J. X., Revenko, A. S., Li, L. B., Gemo, A. T., Chen, H.-W. 2007.ANCCA (ATAD2), an estrogen-regulated AAA+ ATPase coactivator for ER-alpha, is required for coregulator occupancy and chromatin modification. Proc. Nat. Acad. Sci. 104: 18067-18072, incorporated herein by reference in its entirety). PRC1 (Protein regulator of cytokinesis 1) gene encodes for a protein which is key regulator of cytokinesis. It is required to recruit PLK1 and KIF14 to the central spindle. It has been shown to act as an oncogene for promoting cell proliferation, inhibition of apoptosis and tumor progression in bladder cancer (Shimo, A., Nishidate, T., Ohta, T., Fukuda, M., Yusuke Nakamura, Y., Katagiri, T. 2006. Elevated expression of protein regulator of cytokinesis 1, involved in the growth of breast cancer cells. Cancer Sci. 98 (2): 174-181, incorporated herein by reference in its entirety).

An interesting gene found to be downregulated by sub-lethal doses of isopicrinine was NUSAP1 which is involved in mitotic spindle assembly, chromosome segregation during cell division and cytokinesis. A recent study revealed the role of NUSAP1 in BRCA1-regulated pathways of DNA repair and centrosome duplication, which is essential for maintaining genome stability (Kotian, S., Banerjee, T., Lockhart, A., Huang, K., Umit V Catalyurek, U. V., Parvin. J. D. 2014. NUSAP1 influences the DNA damage response by controlling BRCA1 protein levels. Cancer Bio. Thera. 15(5): 533-543, incorporated herein by reference in its entirety). Several studies have demonstrated the over-expression of NUSAP1 in various cancer such as melanoma, prostate, glioblastoma and liver carcinoma (Gulzar, Z. G., McKenney, J. K., Brooks, J. D. 2013. Increased expression of NuSAP in recurrent prostate cancer is mediated by E2F1. Oncogene, 32:70-77, incorporated herein by reference in its entirety). It has been linked to enhanced disease aggression in meningiomas, increased risk in breast cancer patients and development of resistance to chemotherapy in pancreatic cancer patients. It has now been identified as an important biomarker for breast ductal carcinoma and development of drug resistance.

The Ndc80 gene, found to be downregulated by isopicrinine, encodes for a kinetochore protein which is responsible for correct chromosome segregation during mitosis by ensuring the proper bipolar attachment of chromosome. Over-expression of Ndc80 has been shown to induce hepatitis B virus-related hepatocellular carcinoma. RNAi mediated silencing of Ndc80 expression in hepatoma cell line HepG2, resulted in inhibition of cell proliferation and suppressed the replication of hepatitis B virus (Liu, B., Yaoa, Z., Hua, K., Huanga, H., Xua, S., Wanga, Q., Yangb, Y., Ren, J. 2016. ShRNA-mediated silencing of the Ndc80 gene suppresses cell proliferation and affected hepatitis B virus-related hepatocellular carcinoma. Clin. Res. Hepatol. Gastroenterol. 40, 297-303, incorporated herein by reference in its entirety). CDCA5 gene encodes for sororin protein which is required for sister chromatid cohesion in interphase. Phosphorylation and activation of sororin by ERK had been shown to play a key role in cell proliferation in lung cancer (Nguyen, M. H., Koinuma, J., Ueda, K., Ito, T., Tsuchiya, E., Nakamura, Y., Daigo, Y. 2010. Phosphorylation and activation of cell division cycle associated 5 by mitogen-activated protein kinase play a crucial role in human lung carcinogenesis. Cancer Res. 70: 5337-5347; and Tokuzen, N., Nakashiro, K., Tanaka, H., Iwamoto, K., Hamakawa, H. 2015. Therapeutic potential of targeting cell division cycle associated 5 for oral squamous cell carcinoma. Oncotarget, 7(3): 2343-2353, each incorporated herein by reference in their entirety). Aurora B kinase is required for the attachment of mitotic spindle to the centromere during cell division. Over-expression of this kinase leads to unequal chromosomal separation, resulting in abnormal number of chromosomes in the daughter cells, thus causing cancer development (Shannon, K. B., Salmon, E. D. 2002. Chromosome dynamics: New light on dispatch Aurora B kinase function. Curr. Biol. 12: R458-R460; and Fu, J., Bian, M., Jiang, Q., Zhang, C. 2007. Roles of Aurora kinases in mitosis and tumorigenesis. Mol. Cancer Res. 5(1): 1-10, each incorporated herein by reference in their entirety). PTTG1 (pituitary tumor-transforming 1) gene found down-regulated after exposure with isopicrinine, encodes for a protein which inhibit separins from promoting sister chromatid separation. This protein has been shown to have tumorigenic activity in animal models and is also highly upregulated in several tumors (Molina-Jimenez, F., Benedicto, I., Murata, M., Martín-Vílchez, S., Seki, T., Pintor-Toro, J. A., Tortolero, M., Moreno-Otero, R., Okazaki, K., Koike, K., Barbero, J. L., Matsuzaki, K., Majano, P. L., Lopez-Cabrerá M. 2010. Expression of Pituitary tumor-transforming gene1 (PTTG1)/Securin in Hepatitis B virus (HBV)-Associated liver diseases: Evidence for an HBV X protein-mediated inhibition of PTTG1 ubiquitination and degradation. Hepatology, 51: 777-787; and Chen, D. T., Nasir, A., Culhane, A., Venkataramu, C., Fulp, W., Rubio, R., Wang, T., Agrawal, D., McCarthy, S. M., Gruidl, M., et al. 2010. Proliferative genes dominate malignancy-risk gene signature in histologically-normal breast tissue. Breast Cancer Res Treat, 119:335-46, each incorporated herein by reference in their entirety).

The invention claimed is:

1. A pharmaceutical composition comprising:
   at least one of a compound represented by Formula (1), a derivative thereof, a solvate thereof, a salt thereof, a compound represented by Formula (2), a derivative thereof, a solvate thereof, and a salt thereof; and
   at least one exogenous pharmaceutically acceptable carrier and/or excipient which is not present in *Rhazya Stricta*, wherein Formula (1) and Formula (2) are:

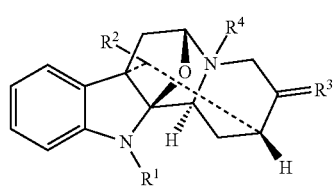

(1)

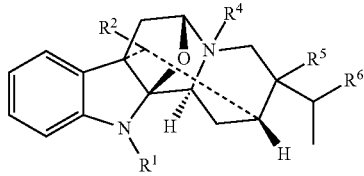

(2)

where $R^1$ is a hydrogen, an optionally substituted alkyl group, an optionally substituted cycloalkyl, an optionally substituted arylalkyl group, an optionally substituted alkanoyl, an optionally substituted aroyl, an optionally substituted alkylsulfonyl, or an optionally substituted arylsulfonyl;

$R^2$ is a carboxy group, a carboxylate group, an optionally substituted alkanoyloxy, an optionally substituted aroyloxy, or an optionally substituted carbamyl;

$R^3$ is O or an optionally substituted $CH_2$;

$R^4$ is a pair of electrons, a hydrogen, an optionally substituted alkyl group, an optionally substituted cycloalkyl, or an optionally substituted arylalkyl group, with the proviso when $R^4$ is an optionally substituted alkyl group, an optionally substituted cycloalkyl, or an optionally substituted arylalkyl group, the nitrogen atom attached to $R^4$ has a positive charge; and $R^5$ and $R^6$ are independently a hydrogen, a halogen, or a hydroxy.

2. The pharmaceutical composition of claim 1, wherein $R^1$ is a hydrogen.

3. The pharmaceutical composition of claim 2, wherein $R^2$ is —$CO_2CH_3$.

4. The pharmaceutical composition of claim 3, wherein $R^4$ is a pair of electrons.

5. The pharmaceutical composition of claim 1, wherein the compound represented by Formula (1) is:

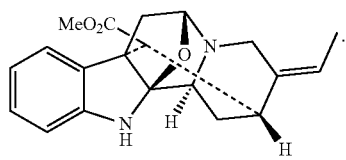 [SMILES: C/C=C1\CN2[C@H]3C[C@@H]1[C@@H](C(=O)OC)[C@]14C[C@H]2O[C@]31Nc1ccccc14]

6. The pharmaceutical composition of claim 1, comprising 0.01-20 wt % of the compound represented by Formula (1) or Formula (2), based on a total weight of the pharmaceutical composition.

7. The pharmaceutical composition of claim 6, comprising 0.1-5 wt % of the compound represented by Formula (1) or Formula (2), based on a total weight of the pharmaceutical composition.

8. The pharmaceutical composition of claim 1, wherein the at least one exogenous pharmaceutically acceptable carrier and/or excipient is selected from the group consisting of an organic solvent, a synthetic polymer, a synthetic fatty ester, a fatty acid, a vegetable oil, and a surfactant.

9. The pharmaceutical composition of claim 8, wherein the at least one exogenous pharmaceutically acceptable carrier and/or excipient is an organic solvent selected from the group consisting of methanol, ethanol, trifluoroethanol, n-propanol, i-propanol, n-butanol, i-butanol, t-butanol, propylene glycol, polyethylene glycol, glycerol, poly(tetramethylene ether) glycol, acetone, butanone, ethyl acetate, propyl acetate, dimethylformamide, dimethylacetamide, pyrrolidone, N-methyl-2-pyrrolidone, N-(2-hydroxyethyl) pyrrolidone, dimethyl sulfoxide, decylmethyl sulfoxide, and tetradecylmethyl sulfoxide.

10. A method of treating cancer in a subject in need thereof, the method comprising:
administering an effective amount of a compound of Formula (1) or Formula (2), a derivative thereof, a solvate thereof, or a combination thereof to the subject, wherein Formula (1) and Formula (2) are:

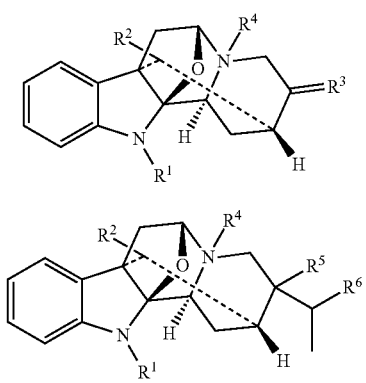

where $R^1$ is a hydrogen, an optionally substituted alkyl group, an optionally substituted cycloalkyl, an optionally substituted arylalkyl group, an optionally substituted alkanoyl, an optionally substituted aroyl, an optionally substituted alkylsulfonyl, or an optionally substituted arylsulfonyl;
$R^2$ is a carboxy group, an optionally substituted alkanoyloxy, an optionally substituted aroyloxy, or an optionally substituted carbamyl;
$R^3$ is O or an optionally substituted $CH_2$;
$R^4$ is a pair of electrons, an optionally substituted alkyl group, an optionally substituted cycloalkyl, or an optionally substituted arylalkyl group, with the proviso when $R^4$ is an optionally substituted alkyl group, an optionally substituted cycloalkyl, or an optionally substituted arylalkyl group, the nitrogen atom attached to $R^4$ has a positive charge; and
$R^5$ and $R^6$ are independently a hydrogen, a halogen, or a hydroxy.

11. The method of claim 10, wherein the cancer is at least one selected from the group consisting of lung cancer, stomach cancer, colon cancer, liver cancer, ovarian cancer, kidney cancer, breast cancer, prostate cancer, uterus cancer, melanoma, esophageal cancer, brain cancer, and pancreatic cancer.

12. The method of claim 11, wherein the cancer is breast cancer and/or pancreatic cancer.

13. The method of claim 10, wherein the effective amount of the compound of Formula (1) or Formula (2), a derivative thereof, a solvate thereof, or a combination thereof is in a range of 1-100 mg/kg body weight of the subject.

14. A method of extracting a compound from *Rhazya Stricta*, the method comprising:
mixing at least a first part of *Rhazya Stricta* or a first extract of *Rhazya Stricta* with a solution comprising water and an acid thereby forming a second extract;
mixing the second extract with an organic solvent thereby forming a first aqueous layer and a first organic layer;
mixing the first aqueous layer with a base thereby forming a neutralized aqueous layer;
mixing the neutralized aqueous layer with the organic solvent thereby forming a second aqueous layer and a second organic layer;
concentrating the second organic layer thereby forming a residue comprising the compound; and
isolating the compound, wherein the compound is:

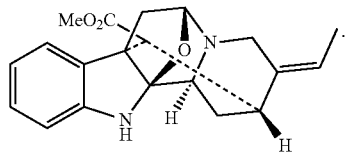 [SMILES: C/C=C1\CN2[C@H]3C[C@@H]1[C@@H](C(=O)OC)[C@]14C[C@H]2O[C@]31Nc1ccccc14]

15. The method of claim 14, wherein the acid is a mineral acid, the organic solvent is a chlorinated organic solvent, and the base comprises hydroxide.

16. The method of claim 14, wherein the first extract is obtained by:
mixing at least a second part of *Rhazya Stricta* with a plurality of organic solvents thereby forming the first extract.

17. The method of claim 16, wherein the plurality of organic solvents comprises a chlorinated organic solvent and an alcohol.

* * * * *